(12) United States Patent
Kemp et al.

(10) Patent No.: US 6,562,964 B1
(45) Date of Patent: May 13, 2003

(54) HETEROCYCLIC COMPOUNDS AS INHIBITORS OF ROTAMASE ENZYMES

(75) Inventors: Mark Ian Kemp, Sandwich (GB); Michael John Palmer, Sandwich (GB); Mark Allen Sanner, Old Saybrook, CT (US); Martin James Wythes, New London, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/056,901

(22) Filed: Jan. 23, 2002

Related U.S. Application Data

(62) Division of application No. 09/358,107, filed on Jul. 21, 1999, now Pat. No. 6,372,736.

(30) Foreign Application Priority Data

Jul. 21, 1998 (GB) .............................................. 9815880

(51) Int. Cl.⁷ .................... C07D 403/00; C07D 471/00; C07D 401/04; C07D 403/02; C07D 235/16
(52) U.S. Cl. ...................... 540/603; 546/64; 546/273.4; 548/306.1; 548/309.1; 548/301.7
(58) Field of Search ............................ 548/306.1, 309.4, 548/301.7; 546/64, 273.4; 540/603

(56) References Cited

U.S. PATENT DOCUMENTS 6,372,736 B1 * 4/2002 Kemp

FOREIGN PATENT DOCUMENTS

WO 98/13355 * 4/1998
WO 00/05232 * 2/2000

* cited by examiner

Primary Examiner—D. Margaret Seaman
(74) Attorney, Agent, or Firm—Peter C. Richardson; Paul H. Ginsburg; E. Victor Donahue

(57) ABSTRACT

Compounds of the formula (I):

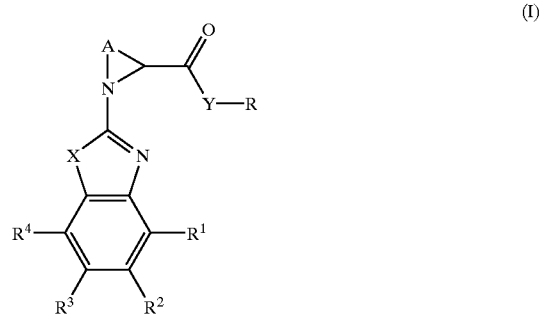

wherein A, Y, R, X, $R^1$, $R^2$, $R^3$ and $R^4$ are as defined above are inhibitors of rotamase enzymes in particular FKBP-12 and FKBP-52. The compounds therefore moderate neuronal regeneration and outgrowth and can be used for treating neurological disorders arising from neurodegenerative diseases or other disorders involving nerve damage.

4 Claims, No Drawings

HETEROCYCLIC COMPOUNDS AS INHIBITORS OF ROTAMASE ENZYMES

This application is a divisional of U.S. patent application Ser. No. 09/358,107, filed Jul. 21, 1999 now U.S. Pat. No. 6,372,736, allowed Oct. 23, 2001, which claims priority from Great Britain Patent Application No. 9815880.1, filed Jul. 21, 1998, which applications are hereby incorporated by reference.

This invention relates to 1-heteroaryl-pyrrolidine, -piperidine and -homopiperidine derivatives and to processes for the preparation of, intermediates used in the preparation of, compositions containing and the uses of, such derivatives.

It has been reported that the immunosuppressant FK-506 promotes neurite outgrowth in vitro in neuronal cell line and culture models (see Lyons et al, Pro. Natl. Acad. Sci., 1994, 91, 3191–95 and Snyder et al, Nature Medicine, 1995, 1, 32–37). WO-A-96/40140, WO-A-96/40633 and WO-A-97/16190 disclose compounds that have neurotrophic activity but which lack inhibitory action at the protein phosphatase calcineurin and therefore which have no immunosuppressive activity. U.S. Pat. No. 5,721,256 discloses sulphonamides, and WO-A-98/13343 and WO-A-98/13355 disclose heterocycles, that have neurotrophic activity but which do not exert any significant immunosuppressive activity. WO-A-92/21313 discloses sulphonamides with immunosuppressive activity.

It has been suggested in WO-A-96/40140 and WO-A-96/40633 that the neurotrophic effect of these compounds is mediated, at least in part, by a high affinity interaction with the FK-506 binding proteins, such as FKBP-12, or FKBP-52. However, the mechanism by which this interaction with FKBP-type immunophilins results in a neurotrophic effect is at present unknown. The range of neurotrophic activity that can be realised through this neurotrophic/non-immunosuppressant class of compounds has been explored and it has been found that axon regeneration can be promoted after facial nerve crush and sciatic nerve crush in the rat. It has also been observed that the functional regeneration of dopamine neurons damaged with the toxin MPTP was promoted by the compounds disclosed therein in mice.

Additionally, it was reported that restoration of striatal innervation in the rat was promoted by the compounds disclosed therein following 6-hydroxydopamine lesioning of dopaminergic neurons (see Hamilton & Steiner, Current Pharmaceutical Design, 1997, 3, 405–428).

It has now been found that the present compounds are neurotrophic agents which have an affinity for FKBP-type immunophilins. In particular, they are potent inhibitors of the enzyme activity and especially of the cis-trans prolyl isomerase (rotamase) activity of FKBP-type immunophilins, particularly the immunophilin FKBP-12. The present compounds do not significantly inhibit the protein phosphatase calcineurin and therefore lack any significant immunosuppressive activity.

The present compounds therefore moderate neuronal degeneration and promote neuronal regeneration and outgrowth and can be used for treating neurological disorders arising from neurodegenerative diseases or other disorders involving nerve damage. The neurological disorders that may be treated include senile dementia (Alzheimer's disease) and other dementias, amyotrophic lateral sclerosis and other forms of motor neuron disease, Parkinson's disease, Huntington's disease, neurological deficits associated with stroke, all forms of degenerative disease affecting the central or peripheral nervous system (e.g. cerebellar-brainstem atrophies, syndromes of progressive ataxias), all forms of muscular dystrophy, progressive muscular atrophies, progressive bulbar muscular atrophy, physical or traumatic damage to the central or peripheral nervous system (e.g. spinal cord), herniated, ruptured or prolapsed intervertebrae disc syndromes, cervical spondylosis, plexus disorders, thoracic outlet syndromes, all forms of peripheral neuropathy (both diabetic and non-diabetic), trigeminal neuralgia, glossopharyngeal neuralgia, Bell's Palsy, all forms of auto-immune related disease resulting in damage of the central or peripheral nervous system (e.g. multiple sclerosis, myasthenia gravis, Guillain-Barré syndrome), AIDS related disorders of the nervous system, dapsone ticks, bulbar and retrobulbar affections of the optic nerve (e.g. retinopathies and retrobulbar neuritis), hearing disorders such as tinnitus, and prion diseases.

Preferably, the present compounds can be used for treating senile dementia (Alzheimer's disease) or another dementia, amyotrophic lateral sclerosis or another form of motor neuron disease, Parkinson's disease, Huntingdon's disease, a neurological deficit associated with stroke, physical or traumatic damage to the central or peripheral nervous system (e.g. spinal cord), a peripheral neuropathy (either diabetic or non-diabetic), multiple sclerosis or a hearing disorder such as tinnitus.

The present invention provides a compound of the formula:

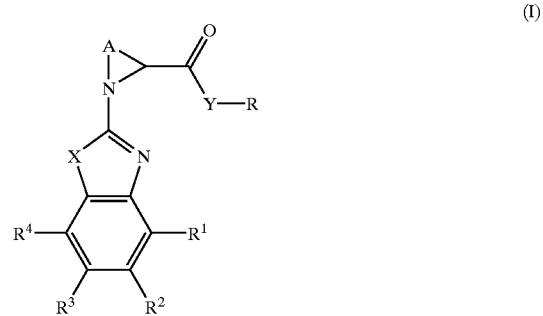

(I)

or a pharmaceutically acceptable salt thereof, wherein

A is unbranched $C_3$–$C_5$ alkylene optionally substituted by $C_1$–$C_6$ alkyl;

X is O, S, NH or N($C_1$–$C_6$ alkyl);

Y is O, S, NH or N($C_1$–$C_6$ alkyl);

R is a C-linked, 4- to 6-membered ring, non-aromatic, heterocyclic group containing one nitrogen heteroatom, said group being optionally substituted by 1, 2 or 3 substituent(s) each independently selected from $C_1$–$C_6$ alkyl, $C_2$–$C_6$ alkenyl, $C_3$–$C_7$ cycloalkyl, aryl, het, —$CO_2$($C_1$–$C_6$ alkyl), —CO(het), —$CONR^5R^6$ and —CO(aryl), said alkyl and alkenyl being optionally substituted by 1 or 2 substituent(s) each independently selected from $C_3$–$C_7$ cycloalkyl, aryl, het, —O(aryl), —O($C_1$–$C_2$ alkylene)aryl, —CO(het), —$CONR^5R^6$ and —CO(aryl);

$R^1$, $R^2$, $R^3$ and $R^4$ are each independently selected from H, halo, $C_1$–$C_6$ alkyl, $C_3$–$C_7$ cycloalkyl, halo($C_1$–$C_6$) alkyl, $C_1$–$C_6$ alkoxy, —$CONR^5R^6$, $C_3$–$C_7$ cycloalkoxy, $C_3$–$C_7$ cycloalkyl-($C_2$–$C_4$)alkylene, $C_3$–$C_7$ cycloalkyl ($C_2$–$C_4$)alkoxy and —$CO_2$($C_1$–$C_6$ alkyl);

$R^5$ and $R^6$ are either each independently selected from H and $C_1$–$C_6$ alkyl or, when taken together, represent unbranched $C_3$–$C_5$ alkylene;

"aryl" means phenyl, optionally substituted by 1, 2 or 3 substituent(s) each independently selected from $C_1$–$C_6$ alkyl, $C_1$–$C_6$ alkoxy, halo, —$CONR^5R^6$, halo($C_1$–$C_6$ alkyl) and —$NR^5R^6$; and "het" means a 5- or 6-membered monocyclic, or 8-, 9- or 10-membered bicyclic, ring heterocyclic group containing from 1 to 3 heteroatoms each independently selected from N, O and S, said group being optionally substituted by 1, 2 or 3 substituent(s) each independently selected from $C_1$–$C_6$ alkyl, $C_1$–$C_6$ alkoxy, halo, halo($C_1$–$C_6$ alkyl), phenyl and —$NR^5R^6$.

Throughout the above definitions, "halo" means fluoro, chloro, bromo or iodo and alkyl, alkoxy, alkenyl and alkylene groups containing the requisite number of carbon atoms, except where indicated, can be unbranched- or branched-chain.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases which form non-toxic salts and examples are the sodium, potassium, aluminium, calcium, magnesium, zinc and diethanolamine salts.

For a review on suitable salts see Berge et al, J. Pharm. Sci., 1977, 66, 1–19.

The pharmaceutically acceptable solvates of the compounds of the formula (I) include the hydrates thereof.

Also included within the present scope of the compounds of the formula (I) are polymorphs and radiolabelled derivatives thereof.

A compound of the formula (I) contains one or more asymmetric carbon atoms and therefore exists in two or more stereoisomeric forms. Where a compound of the formula (I) contains an alkenyl or alkenylene group, cis (E) and trans (Z) isomerism may also occur. The present invention includes the individual stereoisomers of the compounds of the formula (I) and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Particularly preferred are compounds of the formula:

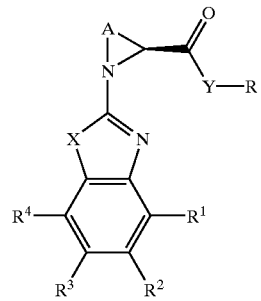

(IA)

wherein R, $R^1$, $R^2$, $R^3$, $R^4$, A, X and Y are as previously defined for a compound of the formula (I).

In the above definitions of a compound of the formula (I) and (IA), the following definitions are preferred.

Preferably, A is 1,4-butylene.
Preferably, X is O, S or NH.
Preferably, X is O or NH.
Preferably, Y is O or NH.
Preferably, Y is NH.
Preferably, R is azetidinyl, pyrrolidinyl or piperidinyl, each optionally substituted as previously defined for R for a compound of the formula (I).

Preferably, R is 3-azetidinyl, 3-pyrrolidinyl, 3-piperidinyl or 4-piperidinyl, each optionally substituted as previously defined for R for a compound of the formula (I).

Preferably, R is azetidinyl, pyrrolidinyl or piperidinyl, each optionally substituted by 1, 2 or 3 substituent(s) each independently selected from $C_1$–$C_6$ alkyl, het, —$CO_2$($C_1$–$C_6$ alkyl) and —CO(het), said alkyl being optionally substituted by 1 or 2 substituent(s) each independently selected from $C_3$–$C_7$ cycloalkyl, aryl, het, —O(aryl), —O($C_1$–$C_2$ alkylene)aryl and —$CONR^5R^6$.

Preferably, R is 3-azetidinyl, 3-pyrrolidinyl, 3-piperidinyl or 4-piperidinyl, each optionally substituted by 1, 2 or 3 substituent(s) each independently selected from $C_1$–$C_6$ alkyl, het, —$CO_2$($C_1$–$C_6$ alkyl) and —CO(het), said alkyl being optionally substituted by 1 or 2 substituent(s) each independently selected from $C_3$–$C_7$ cycloalkyl, aryl, het, —O(aryl), —O($C_1$–$C_2$ alkylene)aryl and —$CONR^5R^6$.

Preferably, R is azetidinyl, pyrrolidinyl or piperidinyl, each optionally substituted by 1, 2 or 3 substituent(s) each independently selected from ethyl, 2-pyridyl, tert-butoxycarbonyl, quinolin-2-ylcarbonyl, 2-phenylquinolin-4-ylcarbonyl, 4-methoxyquinolin-2-ylcarbonyl, 6-methoxy-2-phenylquinolin-4-ylcarbonyl, 2-piperidinoquinolin-4-ylcarbonyl, 2-chloroquinolin-4-ylcarbonyl, 1H-benzpyrazol-6-ylcarbonyl, cyclopropylmethyl, phenylmethyl, diphenylmethyl, 2-pyridylmethyl, 3-pyridylmethyl, 4-pyridylmethyl, 2-(2-pyridyl)ethyl, 2-(2-methylimidazol-1-yl)ethyl, (1H-1,2,4-triazol-3-yl)methyl, (2-chloroquinolin-3-yl)methyl, quinolin-4-ylmethyl, quinolin-2-ylmethyl, quinolin-3-ylmethyl, 1-(quinolin-4-yl) ethyl, (2-fluoropyridin-4-yl)methyl, phenoxymethyl, benzyloxymethyl, aminocarbonylmethyl, 2-(aminocarbonyl)ethyl and 3-(aminocarbonyl) phenylmethyl.

Preferably R is 3-azetidinyl, 3-pyrrolidinyl, 3-piperidinyl or 4-piperidinyl, each optionally substituted by 1, 2 or 3 substituent(s) each independently selected from ethyl, 2-pyridyl, tert-butoxycarbonyl, quinolin-2-ylcarbonyl, 2-phenylquinolin-4-ylcarbonyl, 4-methoxyquinolin-2-ylcarbonyl, 6-methoxy-2-phenylquinolin-4-ylcarbonyl, 2-piperidinoquinolin-4-ylcarbonyl, 2-chloroquinolin-4-ylcarbonyl, 1H-benzpyrazol-6-ylcarbonyl, cyclopropylmethyl, phenylmethyl, diphenylmethyl, 2-pyridylmethyl, 3-pyridylmethyl, 4-pyridylmethyl, 2-(2-pyridyl)ethyl, 2-(2-methylimidazol-1-yl)ethyl, (1H-1,2,4-triazol-3-yl)methyl, (2-chloroquinolin-3-yl)methyl, quinolin-4-ylmethyl, quinolin-2-ylmethyl, quinolin-3-ylmethyl, 1-(quinolin-4-yl)ethyl, (2-fluoropyridin-4-yl)methyl, phenoxymethyl, benzyloxymethyl, aminocarbonylmethyl, 2-(aminocarbonyl)ethyl and 3-(aminocarbonyl) phenyl methyl.

Preferably, $R^1$, $R^2$, $R^3$ and $R^4$ are each independently selected from H, halo($C_1$–$C_6$)alkyl and halo.

Preferably, $R^1$, $R^2$, $R^3$ and $R^4$ are each independently selected from H, fluoro, chloro, bromo and trifluoromethyl.

Preferably, $R^5$ and $R^6$ are either each H or, when taken together, are 1,5-pentylene.

Preferably, "aryl" means a phenyl group, optionally substituted by $CONR^5R^6$, wherein $R^5$ and $R^6$ are preferably both H.

Preferably, "het" means pyridyl, imidazolyl, triazolyl, quinolinyl or benzpyrazolyl, each optionally substituted by 1, 2 or 3 substituent(s) each independently selected from $C_1$–$C_6$ alkyl, $C_1$–$C_6$ alkoxy, halo, phenyl and —$NR^5R^6$.

Preferably, "het" means pyridyl, imidazolyl, triazolyl, quinolinyl or benzpyrazolyl, each optionally substituted by 1, 2 or 3 substituent(s) each independently selected from methyl, methoxy, fluoro, chloro, phenyl and piperidino.

Preferably, "het" means 2-pyridyl, 3-pyridyl, 4-pyridyl, imidazol-1-yl, 1H-1,2,4-triazol-3-yl, quinolin-2-yl, quinolin-3-yl, quinolin-4-yl or 1H-benzpyrazol-6-yl, each optionally substituted by 1, 2 or 3 substituent(s) each independently selected from $C_1$–$C_6$ alkyl, $C_1$–$C_6$ alkoxy; halo, phenyl and —$NR^5R^6$.

Preferably, "het" means 2-pyridyl, 3-pyridyl, 4-pyridyl, imidazol-1-yl, 1H-1,2,4-triazol-3-yl, quinolin-2-yl, quinolin-3-yl, quinolin-4-yl or 1H-benzpyrazol-6-yl, each optionally substituted by 1,2 or 3 substituent(s) each independently selected from methyl, methoxy, fluoro, chloro, phenyl and piperidino.

Preferably, "het" means 2-pyridyl, 3-pyridyl, 4-pyridyl, 1H-1,2,4-triazol-3-yl, quinolin-2-yl, quinolin-3-yl, quinolin-4-yl, 1H-benzpyrazol-6-yl, 2-methylimidazol-1-yl, 2-chloroquinolin-3-yl, 2-phenylquinolin-4-yl, 4-methoxyquinolin-2-yl, 6-methoxy-2-phenylquinolin-4-yl, 2-piperidinoquinolin-4-yl, 2-chloroquinolin-4-yl or 2-fluoropyridin-4-yl.

Preferably, the group of the formula:

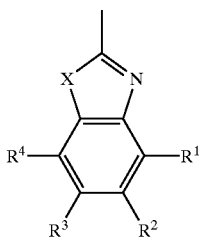

in a compound of the formula (I) is 1,3-benzoxazol-2-yl, 1,3-benzothiazol-2-yl, 1H-benzimidazol-2-yl, 6-bromo-1,3-benzoxazol-2-yl or 6-chloro-1,3-benzothiazol-2-yl.

Particularly preferred examples of the compounds of the formula (I) as described in the Examples section hereafter are:

(2S)-1-(1,3-Benzoxazol-2-yl)-$N^2$-[(3S)-1-benzylpyrrolidin-3-yl]-2-piperidinecarboxamide;

(2S)-1-(1,3-Benzoxazol-2-yl)-$N^2$-[(3S)-1-(2-pyridinylmethyl)pyrrolidin-3-yl]-2-piperidinecarboxamide;

(2S)-1-(1,3-Benzoxazol-2-yl)-$N^2$-[(3S)-1-(3-pyridinylmethyl)pyrrolidin-3-yl]-2-piperidinecarboxamide;

(2S)-1-(1,3-Benzoxazol-2-yl)-$N^2$-[(3S)-1-(4-pyridinylmethyl)pyrrolidin-3-yl]-2-piperidinecarboxamide;

(2S)-$N^2$-{(3S)-1-[3-(Aminocarbonyl)phenylmethyl]pyrroidin-3-yl}-1-(1,3-benzoxazol-2-yl)-2-piperidinecarboxamide;

(2S)-$N^2$-{(3S)-1-[(2-Chlorooquinolin-3-yl)methyl)]pyrrolidin-3-yl}-1-(1,3-benzoxazol-2-yl)-2-piperidinecarboxamide;

(2S)-$N^2$-{(3S)-1-[(Quinolin-3-yl)methyl)]pyrrolidin-3-yl}-1-(1,3-benzoxazol-2-yl)-2-piperidinecarboxamide;

(2S)-$N^2$-{(3S)-1-[(Quinolin-4-yl)methyl)]pyrrolidin-3-yl}-1-(1,3-benzoxazol-2-yl)-2-piperidinecarboxamide;

(2S)-$N^2$-{(3S)-1-[(Quinolin-2-yl)methyl)]pyrrolidin-3-yl}-1-(1,3-benzoxazol-2-yl)-2-piperidinecarboxamide;

(2S)-$N^2$-{(3S)-1-[1-(Quinolin-4-yl)ethyl)]pyrrolidin-3-yl}-1-(1,3-benzoxazol-2-yl)-2-piperidinecarboxamide;

(2S)-N-{(3S)-1-[Quinolin-2-ylcarbonyl]pyrrolidin-3-yl}-1-(1,3-benzoxazol-2-yl)-2-piperidinecarboxamide;

(2S)-$N^2$-{(3S)-1-[2-Phenylquinolin-4-ylcarbonyl]pyrrolidin-3-yl}-1-(1,3-benzoxazol-2-yl)-2-piperidinecarboxamide;

(2S)-$N^2$-{(3S)-1-[4-Methoxyquinolin-2-ylcarbonyl]pyrrolidin-3-yl}-1-(1,3-benzoxazol-2-yl)-2-piperidinecarboxamide;

(2S)-$N^2$-{(3S)-1-[6-Methoxy-2-phenylquinolin-4-ylcarbonyl]pyrrolidin-3-yl}1-(1,3-benzoxazol-2-yl)-2-piperidinecarboxamide;

(2S)-$N^2$-{(3S)-1-[2-Piperidinoquinoin-4-ylcarbonyl]pyrrolidin-3-yl}-1-(1,3-benzoxazol-2-yl)-2-piperidinecarboxamide;

(2S)-$N^2$-{(3S)-1-[2-Chloroquinolin-4-ylcarbonyl]pyrrolidin-3-yl}-1-(1,3-benzoxazol-2-yl)-2-piperidinecarboxamide;

(2S)-$N^2$-{(3S)-1-[1H-benzpyrazol-6-ylcarbonyl]pyrrolidin-3-yl}-1-(1,3-benzoxazol-2-yl)-2-piperidinecarboxamide;

(2S)-$N^2$-[(3S)-1-Benzylpyrrolidin-3-yl]-1-(6-bromo-1,3-benzoxazol-2-yl)-2-piperidinecarboxamide;

(2S)-1-(1,3-Benzoxazol-2-yl)-$N^2$-(1-benzyl-3-piperidinyl)-2-piperidinecarboxamide;

(2S)-1-(1,3-Benzoxazol-2-yl)-$N^2$-(3R,5S)-5-[(benzyloxy)methyl]pyrrolidin-3-yl-2-piperidinecarboxamide hydrochloride; and 1-(1H-1,3-Benzimidazol-2-yl)-$N^2$-[(3S)-1-benzylpyrrolidin-3-yl]-2-piperidinecarboxamide.

The compounds of the formula (I) can be prepared using conventional procedures such as by the following illustrative methods in which R, $R^1$, $R^2$, $R^3$, $R^4$, A, X and Y are as previously defined for a compound of the formula (I) unless otherwise stated.

1) Compounds of the formula (I) wherein X is O or S can be prepared by dehydrative coupling of a compound of the formula:

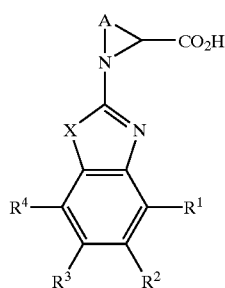

(II)

wherein X is O or S with a compound of the formula:

H—Y—R     (III)

Compounds having the formula (II) can be prepared according to the method illustrated in Preparation 3 as detailed herein. Suitable conditions for such preparations use conventional procedures well known to the skilled person such as those referred to in standard texts, e.g. see Advanced Organic Chemistry, Third Edition, Jerry March, 0-56, p. 371–4.

Examples of suitable conditions are as follows:

(a) a compound of the formula (II) may be first converted to an activated ester using 1-hydroxybenzotriazole hydrate and 1-(3-dimethylaminopropyl)-3-ethylcarbodiimide hydrochloride in the presence of a suitable acid acceptor, e.g. triethylamine, and then treated in situ with a compound of the formula (III). The reaction may be carried out in a suitable solvent such as dichloromethane. A catalytic amount of a suitable catalyst, e.g. 4-diethylaminopyridine, may also be used.

(b) compounds of the formula (II) and (III) may be combined with triphenylphosphine and diethyl azodicarboxylate in the presence of a suitable solvent such as tetrahydrofuran.

(c) compounds of the formulae (II) and (III) may be combined with 1,1'-carbonyldiimidazole in the presence of a suitable solvent such as tetrahydrofuran or dichloromethane.

(d) directly heating together compounds of the formulae (II) and (III) optionally in the presence of a suitable solvent, e.g. N,N-dimethylacetamide, cyclopentanol or diphenylether, and optionally in the presence of a suitable acidic catalyst, e.g., where Y is O.

The intermediate compounds of the formula (II) may be prepared by conventional methods, for example, by the route shown in Scheme 1.

Scheme 1

(IV)

Esterfication
(e.g. thionyl chloride, methanol)

↓

-continued (V)

N-Substitution using (VI)
(e.g. for X = O, using ethyl-diisopropylamine/acetonitrile or N,N-dimethyl-acetamide/heat,
and for X = S, using copper powder/triethylamine hydrochloride/xylene/heat)

(VI)

↓

(VII)

Hydrolysis
(e.g. aqueous lithium hydroxide, methanol)

↓

(II)

wherein $R^7$ is $C_1$–$C_4$ alkyl, preferably methyl, or benzyl and $L^1$ is a suitable leaving group, e.g. halo (preferably, chloro), —$SCH_3$, —SH, —$SO_2CH_3$, —$SO_2CF_3$, —$OSO_2CH_3$ or —$OSO_2CF_3$.

The compounds of the formulae (III), (IV) and (VI) may be prepared by conventional procedures.

2) Compounds of the formula (I) where X=NH (i.e. a compound of the formula (IB)) may be prepared by the route shown in Scheme 2, that is by reaction of a compound of the formula (XIIIA) or (XIIIB) with a compound of the formula (III).

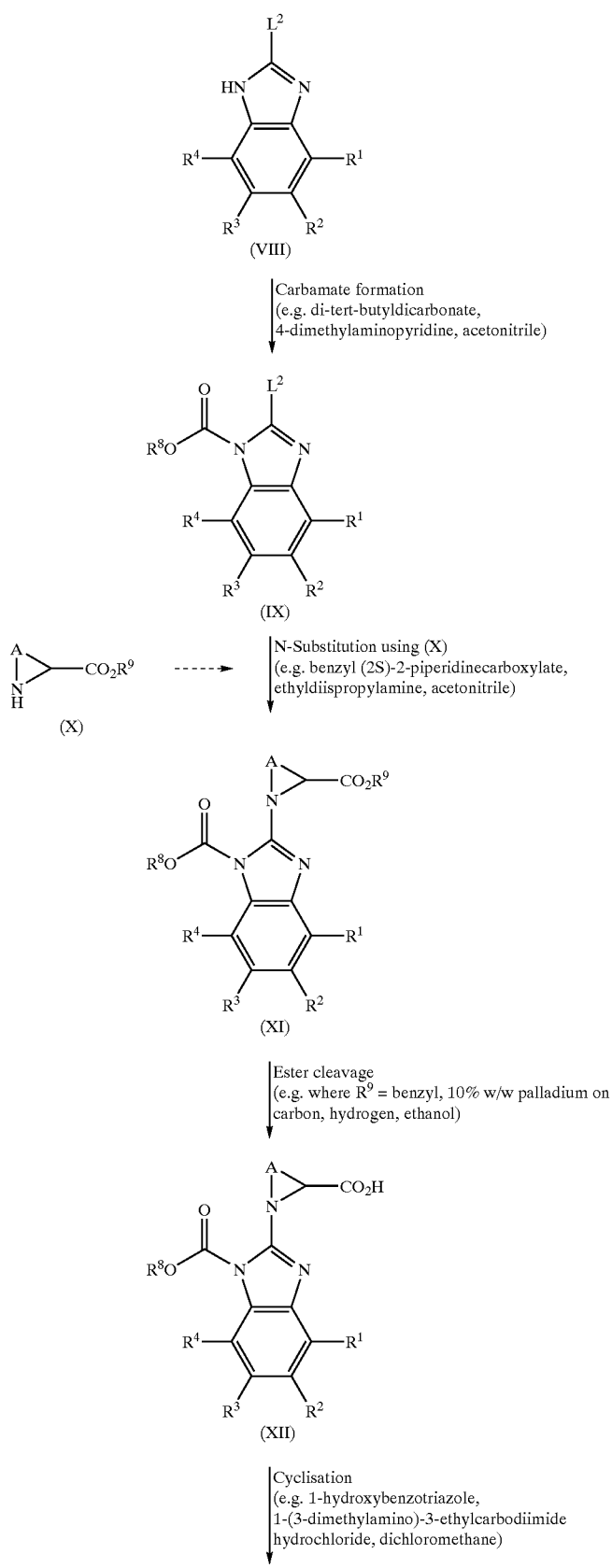

-continued

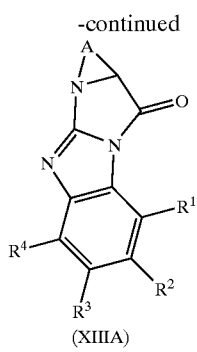

(XIIIA)

and/or

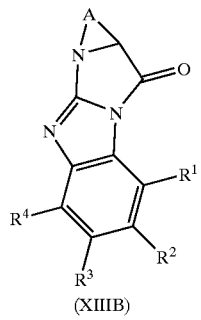

(XIIIB)

H—Y—R  Addition by (III)
(III)   (e.g. 1,4-dioxane, heat)

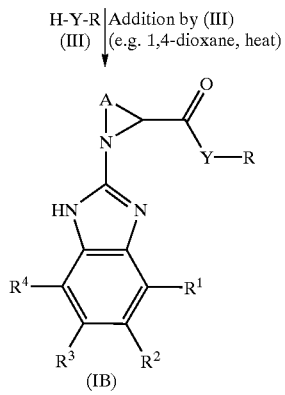

(IB)

wherein $L^2$ is a suitable leaving group, e.g. as previously defined for $L^1$, $R^8$ is $C_1$–$C_4$ alkyl (preferably, t-butyl) or benzyl, and
$R^9$ is $C_1$–$C_4$ alkyl or benzyl.

The compounds of the formulae (VIII) and (X) may be prepared by conventional procedures. Reactions using commercially available compounds having the formulae (VIII) and (X) are provided in Preparations 46 and 47.

3) The compounds of the formula (I) wherein X is O or S can be prepared by reaction of a compound of the formula:

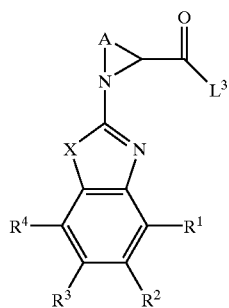

(XIV)

wherein X is O or S, with a compound of the formula:

H—Y—R  (III)

wherein $L^3$ is a suitable leaving group such as
   (i) halo, preferably chloro or bromo,
   (ii) a group providing an activated ester such as that derived by reaction of a compound of the formula (II) with 1-hydroxybenzotriazole, benzotriazol-1-yloxytris(dimethylamino)-phosphonium hexafluorophosphate, O-(1H-benzotriazol-1-yl)-N,N,N',N'-tetramethyluronium tetrafluoroborate, or pentafluorophenol,
   (iii) a group providing a mixed anhydride such as that derived by reaction of a compound of the formula (II) with isobutyl chloroformate,
   or (iv) a group providing an imidazolide such as that derived by reaction of a compound of the formula (II) with 1,1'-carbonyldiimidazole.

The reaction may be performed using standard techniques.

Compounds of the formula (XIV) may be prepared by conventional procedures such as from compounds of the formula (II).

4) All compounds of the formula (I) can be prepared by reaction of a compound of the formula:

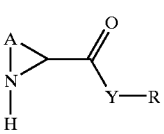

(XV)

with a compound of the formula:

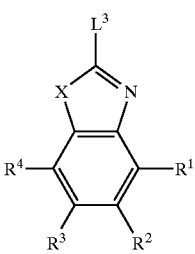

(XVI)

wherein $L^3$ is as previously defined for $L^1$ for a compound of the formula (VI) and preferably is chloro.

In a preferred procedure, where $L^3$ is chloro, the reaction may be carried out in the presence of a suitable acid acceptor, e.g. ethyidiisopropylamine, and in a suitable solvent, e.g. acetonitrile or N,N-dimethylacetamide, with heating.

Where X=S, the reaction may be conveniently carried out using copper powder, triethylamine hydrochloride and xylene with heating.

The compounds of the formula (XV) may be prepared by conventional procedures similar to those described in Preparation 47 herein. The compounds of the formula (XVI) may be prepared by conventional procedures such as are described in Preparation 47 herein.

It will be appreciated that certain compounds of the formula (I) can be converted to other compounds of the formula (I) by conventional methods, e.g. using standard interconversion techniques. All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the Examples and Preparations hereto. It will be appreciated by persons skilled in the art that, within certain of the processes described, the order of the synthetic steps employed may be-varied and will depend inter alia on factors such as the nature of other functional groups present in a particular substrate, the availability of key intermediates and the protecting group strategy (if any) to be employed. Clearly such factors will influence the choice of reagent for use in said synthetic steps.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The affinity of the compounds of the formula (I) for FKBP-12 can be determined in vitro in a coupled colorimetric PPIase assay using similar procedures to published methods (e.g. see Kofron, J. L., et al., Biochemistry, 1991, 30, 6127–6134, Zarnt, T., et al., Biochem. J. 1995, 305, 159–164, Holt, D. A., et al., J. Am. Chem. Soc., 1993, 115,9925–9938). In these methods, the cis-trans isomerisation of a hydrophobic amino acid-proline bond in a tetrapeptide substrate (e.g. the phenylalanine-proline bond in N-succinyl-ala-phe-pro-phe-p-nitroanilide [succinyl-AFPF-pNA]) can be determined by monitoring cleavage of pNA from the transPro-containing peptide by an excess of chymotrypsin.

The $IC_{50}$ (the concentration of the compound of the formula (I) producing 50% inhibition) values were determined using the following assay methodology. Assay buffer (2.175 ml) (50 mM 4-(2-hydroxyethyl)-1-piperazineethanesulphonic acid (HEPES), 100 mM NaCl, 1 mM dithiothreitol (DTT), pH 8.0) is equilibrated to 10° C. in a cuvette. 12.5 $\mu$l of a solution of the present compound in DMSO, 250 $\mu$l of a 60 mg/ml solution of $\alpha$-chymotrypsin in 1 mM aqueous hydrochloric acid and then 50 $\mu$l of a solution of human recombinant FKBP-12 (4.5 $\mu$M) in assay buffer are added and mixed. The reaction is initiated by addition of 12.5 $\mu$l of a solution of 20 mM succinyl-AFPF-pNA in DMSO. The absorbance at 390 nM is monitored for one minute collecting data every 0.25 second. Data are fitted with a first order rate equation with offset and the rate constant obtained corrected for the rate of uncatalysed isomerisation of the substrate. The rate constant determined at different inhibitor concentrations (10 nM to 100 $\mu$M) is expressed as % inhibition of the control rate constant. The $IC_{50}$ is estimated using a non-linear least squares curve fitting routine of the sigmoidal dose response data.

$K_{i,app}$ (the apparent inhibition constant) was determined for the present compounds using the assay procedure described below. Assay buffer (2.175 ml) (50 mM HEPES, 100 mM NaCl, 1 mM DTT, pH 8.0) is equilibrated to 10° C. in a cuvette. 12.5 $\mu$l of a solution of the present compound in DMSO, 250 $\mu$l of a 60 mg/ml solution of $\alpha$-chymotrypsin in 1 mM aqueous hydrochloric acid and then 50 $\mu$L of a solution of human recombinant FKBP-12 (1.5 $\mu$M) in assay buffer are added and mixed. The reaction is initiated by adding 12.5 $\mu$l of a solution of anhydrous succinyl-ALPF-pNA (100 $\mu$M final concentration) in a 400 mM solution of LiCl in trifluoroethanol. The absorbance at 390 nM is monitored for 3 minutes collecting data every 0.5 second. Data are fitted with a first order rate equation with offset and the initial velocity (v) is calculated from the concentration of cis (re leu-pro bond)-succinyl-ALPF-pNA at $t_o$ and the first order rate constant at different inhibitor concentrations (I). Data in the form $v_{inh}/v_{control}$ v. [I] are fitted with an equation for reversible tight binding inhibition to generate values for $K_{i,app}$ (see Morrison, J. F., et al, Comments Mol. Cell Biophys., 1985, 2, 347–368). This analysis is used when the $K_{i,app}$ approaches the concentration of FKBP-12 in the assay (30 nM). Dixon analysis (see Dixon, M., Biochem. J.,1953, 55, 170–171) is used for generating values of $K_{i,app}$ for less potent compounds. The same methodology is used to generate $K_{i,app}$ for FKBP52 with the following modifications: Forty microlitres human recombinant FKBP52 (5.2 $\mu$M) is substituted for FKBP12 and 2.185 ml assay buffer are used in the assay.

The compounds of the invention have inhibitory activity against the FKBP-12 enzyme. Early experimentation suggests that the compounds of the invention also have inhibitory activity against the FKPB-52 enzyme.

The FKBP-52 enzyme can be expressed and characterised by the methodology described in Peattie, D. A., et al, Proc. Natl. Acad. Sci. USA 1992 November 15; 89 (22):10974–8. The FKPB-52 enzyme is discussed in the following references: Miyata, Y., et al, Proc. Natl. Acad. Sci. USA 1997 December 23; 94(26): 14500–5; Tai, P. K., et al, Biochemistry 1993 August 31; 32(34): 8842–7; Bose, S. et al, Science, 274, 1715–5, 1996 and Czar, M. J., et al, Molecular Endocrinology 9, 1549–1560, 1995.

The neurite outgrowth promoting activity of the compounds of the formula (I) can be determined in explant cultures of embryonic chick dorsal root ganglia. Dorsal root ganglia (DRG) are isolated aseptically according to the method of Bray (see "Culturing Nerve Cells", Ed. G. Banker and K. Goslin, MIT Press, Cambridge, Mass., 1991, p.119). The individual ganglia were kept in $Ca^{2+}/Mg^{2+}$-free Tyrodes buffer on ice until a number of ganglia had been collected. Individual ganglia were then transferred into collagen-coated 24-well culture plates containing Neurobasal medium plus B27 supplements and incubated at 37° C. in a 5% $CO_2$ atmosphere. The present compound was added after allowing 4 hours for the ganglia to attach. The explants were fixed and stained with Coomassie blue after 24 or 48 hours in culture. For each treatment 4 to 6 ganglia were analysed and scored by estimating the extent of neurite outgrowth relative to the diameter of the explant using image analysis. The present compounds were tested with and without 10 ng/ml nerve growth factor (NGF) present and compared to outgrowth in the presence of 10 ng/ml nerve growth factor alone.

An alternative system for measuring neurite outgrowth promoting activity of FKBP-12 PPlase inhibitors is the SH-SY-5Y neuroblastoma model described by Gold, B. G., et al, in Exp. Neurol., 1997, 147(2), 269–278. Cells are maintained in Dulbecco's Modified Eagle's Medium (DMEM) supplemented with 10% Foetal calf serum (FCS), 50 U/ml penicillin, 50 µg/ml streptomycin at 37° C. in a 7% $CO_2$ atmosphere. Cells are plated at $1\times10^6$ cells per well and treated for 5 days with 400 nM aphidicolin. Cells are then washed and treated with NGF at 10 ng/ml±various compound concentrations for 7 days to determine if the compounds promote neurite outgrowth in the presence of suboptimal NGF concentrations (and/or in the absence of NGF). Neurite outgrowth is determined by using image analysis to measure neurite lengths in 20 random fields.

The neurotrophic activity of the present compounds can be evaluated in vivo using the sciatic nerve crush model in rat as a model for peripheral nerve regeneration (see Bridge, P. M., et al., Experimental Neurology, 1994, 127, 284–290, Medinaceli, L., et al., Expl. Neurology, 1982, 77, 634–643, Gold, B. G.,et al., Restorative Neurology and Neuroscience, 1994, 6, 287–296), the 1-methyl-4-phenyl-1,2,3,6-tetrahydropyridine (MPTP) and 6-hydroxydopamine models in various species as a model for regeneration in Parkinson's disease (see Mokry, J., Physiol. Res., 1995, 44(3), 143–150) and fimbria-fornix lesions as a model for regeneration in Alzheimer's disease (see Cassel, J. C., Duconseille, E., Jeltsch, H. and Will, B., Prog. Neurol., 1997, 51, 663–716).

The compounds of the formula (I) can be administered alone but will generally be administered in admixture with a suitable pharmaceutical excipient, diluent or carrier selected with regard to the intended route of administration and standard pharmaceutical practice.

For example, the compounds of the formula (I) can be administered orally or sublingually in the form of tablets, capsules, ovules, elixirs, solutions or suspensions, which may contain flavouring or colouring agents, for immediate or controlled release applications.

Such tablets may contain excipients such as microcrystalline cellulose, lactose, sodium citrate, calcium carbonate, dicalcium phosphate and glycine, disintegrants such as starch (preferably corn, potato or tapioca starch), alginic acid and certain complex silicates, and granulation binders such as polyvinylpyrrolidone, sucrose, gelatin and acacia. Additionally, lubricating agents such as magnesium stearate, sodium lauryl sulfate and talc may be included.

Solid compositions of a similar type may also be employed as fillers in gelatin capsules. Preferred excipients in this regard include lactose or milk sugar as well as high molecular weight polyethylene glycols. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol and glycerin, and combinations thereof.

The compounds of the formula (I) can also be injected parenterally, for example, intravenously, intraperitoneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the formula (I) will usually be from 1 microgram/kg to 25 mg/kg (in single or divided doses).

Thus tablets or capsules of the compound of the formula (I) may contain from 0.05 mg to 1.0 g of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of formula (I) can also be administered intranasally or by inhalation and are conveniently delivered in the form of a dry powder inhaler or an aerosol spray presentation from a pressurised container or a nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark] or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the formula (I) and a suitable powder base such as lactose or starch.

Aerosol or dry powder formulations are preferably arranged so that each metered dose or "puff" contains from 20 µg to 20 mg of a compound of the formula (I) for delivery to the patient. The overall daily dose with an aerosol will be in the range of from 20 µg to 20 mg which may be administered in a single dose or, more usually, in divided doses throughout the day.

Alternatively, the compounds of the formula (I) can be administered in the form of a suppository or pessary, or they may be applied topically in the form of a lotion, solution, cream, ointment or dusting powder. The compounds of the formula (I) may also be transdermally administered by the use of a skin patch. They may also be administered by the ocular route, particularly for treating neurological disorders of the eye.

For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the formula (I) can also be administered together with other neurotrophic agents such as neurotrophic growth factor (NGF), glial derived growth factor, brain derived growth factor, ciliary neurotrophic factor and/or neurotrophin-3. The dosage level of the neurotrophic agent will depend upon the neurotrophic effectiveness of the combination and the route of administration used.

It is to be appreciated that all references herein to treatment include curative, palliative and prophylactic treatment.

Thus the invention further provides:

(i) a pharmaceutical composition comprising a compound of the formula (I) or a pharmaceutically acceptable salt or solvate thereof, together with a pharmaceutically acceptable excipient, diluent or carrier;

(ii) a compound of the formula (I), or a pharmaceutically acceptable salt, solvate or composition thereof, for use as a medicament;

(iii) the use of a compound of the formula (I), or of a pharmaceutically acceptable salt, solvate or composition thereof, for the manufacture of a medicament for the treatment of neuronal degeneration;

(iv) the use of a compound of the formula (I), or of a pharmaceutically acceptable salt, solvate or composition thereof, for the manufacture of a medicament for the promotion of neuronal regeneration and outgrowth;

(v) the use of a compound of the formula (I) or of a pharmaceutically acceptable salt, solvate or composition thereof, for the manufacture of a medicament for the treatment of a neurological disease or disorder such as a neurodegenerative disease;

(vi) use as in (v) where the neurological disease or disorder is selected from the group consisting of senile dementia (Alzheimer's disease) and other dementias, amyotrophic lateral sclerosis and other forms of motor neuron disease, Parkinson's disease, Huntington's disease, neurological deficits associated with stroke, all forms of degenerative disease affecting the central or peripheral nervous system (e.g. cerebellar-brainstem atrophies, syndromes of progressive ataxias), all forms of muscular dystrophy, progressive muscular atrophies, progressive bulbar muscular atrophy, physical or traumatic damage to the central or peripheral nervous system (e.g. spinal cord), herniated, ruptured or prolapsed intervertebrae disc syndromes, cervical spondylosis, plexus disorders, thoracic outlet syndromes, all forms of peripheral neuropathy (both diabetic and non-diabetic), trigeminal neuralgia, glossopharyngeal neuralgia, Bell's Palsy, all forms of auto-immune related disease resulting in damage of the central or peripheral nervous system (e.g. multiple sclerosis, myasthenia gravis, Guillain-Barré syndrome), AIDS related disorders of the nervous system, dapsone ticks, bulbar and retrobulbar affections of the optic nerve (e.g. retinopathies and retrobulbar neuritis), hearing disorders such as tinnitus, and prion diseases;

(vii) use as (vi) where the neurological disease or disorder is senile dementia (Alzheimer's disease) or another dementia, amyotrophic lateral sclerosis or another form of motor neuron disease, Parkinson's disease, Huntington's disease, a neurological deficit associated with stroke, physical or traumatic damage to the central or peripheral nervous system (e.g. spinal cord), a peripheral neuropathy (either diabetic or non-diabetic), multiple sclerosis or a hearing disorder such as tinnitus;

(viii) a method of treatment of a human to treat neuronal degeneration which comprises treating said human with an effective amount of a compound of the formula (I) or with a pharmaceutically acceptable salt, solvate or composition thereof;

(ix) a method of treatment of a human to promote neuronal regeneration and outgrowth which comprises treating said human with an effective amount of a compound of the formula (I) or with a pharmaceutically acceptable salt, solvate or composition thereof;

(x) a method of treatment of a human to treat a neurological disease or disorder such as a neurodegenerative disease which comprises treating said human with an effective amount of a compound of the formula (I) or with a pharmaceutically acceptable salt, solvate or composition thereof;

(xi) a method as in (x) where the neurological disease or disorder is selected from the group consisting of senile dementia (Alzheimer's disease) and other dementias, amyotrophic lateral sclerosis and other forms of motor neuron disease, Parkinson's disease, Huntington's disease, neurological deficits associated with stroke, all forms of degenerative disease affecting the central or peripheral nervous system (e.g. cerebellar-brainstem atrophies, syndromes of progressive ataxias), all forms of muscular dystrophy, progressive muscular atrophies, progressive bulbar muscular atrophy, physical or traumatic damage to the central or peripheral nervous system (e.g. spinal cord), herniated, ruptured or prolapsed intervertebrae disc syndromes, cervical spondylosis, plexus disorders, thoracic outlet syndromes, all forms of peripheral neuropathy (both diabetic and non-diabetic), trigeminal neuralgia, glossopharyngeal neuralgia, Bell's Palsy, all forms of auto-immune related disease resulting in damage of the central or peripheral nervous system (e.g. multiple sclerosis, myasthenia gravis, Guillain-Barré syndrome), AIDS related disorders of the nervous system, dapsone ticks, bulbar and retrobulbar affections of the optic nerve (e.g. retinopathies and retrobulbar neuritis), hearing disorders such as tinnitus, and prion diseases;

(xii) a method as in (xi) where the neurological disease or disorder is senile dementia (Alzheimer's disease) or another dementia, amyotrophic lateral sclerosis or another form of motor neuron disease, Parkinson's disease, Huntington's disease, a neurological deficit associated with stroke, physical or traumatic damage to the central or peripheral nervous system (e.g. spinal cord), a peripheral neuropathy (either diabetic or non-diabetic), multiple sclerosis or a hearing disorder such as tinnitus; and (xiii) any novel intermediates described herein.

(xiv) the use of a compound of the formula (I) or of a pharmaceutically acceptable salt, solvate or composition thereof, for the manufacture of a medicament for the treatment of a disease resulting from a deficiency or over production of FKBP-12 or FKBP-52.

The following Examples illustrate the preparation of the compounds of the formula (I). The ACD/IUPAC Pro software programme was used as the basis for naming the prepared compounds.

EXAMPLE 1

(2S)-1-(1,3-Benzoxazol-2-yl)-N$^2$-[(3R)-1-benzylpyrrolidin-3-yl]-2-piperidinecarboxamide

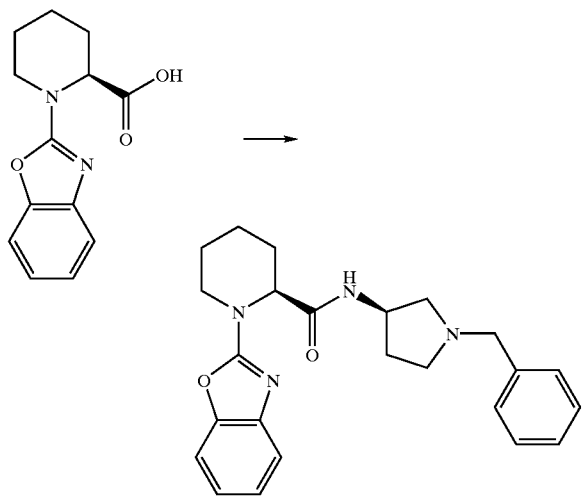

Triethylamine (0.167 ml) was added to a solution of (2S)-1-(1,3-benzoxazol-2-yl)-2-piperidinecarboxylic acid (100 mg) [see Preparation 3], 1-hydroxybenzotriazole hydrate (60.4 mg), (3R)-1-benzylpyrrolidin-3-ylamine (78.7 mg) and 1-(3-dimethylaminopropyl)-3-ethylcarbodiimide hydrochloride (85.4 mg) in dichloromethane (30 ml). The reaction mixture was stirred at room temperature for 18 hours, after which time the mixture was diluted with water and the organic layer was separated, dried over anhydrous sodium sulphate and the solvent removed under reduced pressure. The crude product was purified by column chromatography on silica gel eluting with a solvent gradient of 50:50:0, changing to 25:75:0, changing to 20:80:1, by volume, hexane:ethyl acetate:0.88 aqueous ammonia solution to afford (2S)-1-(1,3-benzoxazol-2-yl)-N$^2$-[(3R)-1-benzylpyrrolidin-3-yl]-2-piperidinecarboxamide as a yellow oil (94 mg).

$^1$H-NMR (CDCl$_3$) δ: 7.40 (1H, d), 7.30–7.20 (7H, m), 7.10 (1H, m), 6.70 (1H, d), 4.90 (1H, s), 4.45 (1H, m), 4.25 (1H, d), 3.70–3.50 (2H, m), 3.20 (1H, t), 2.80 (1H, m), 2.50 (2H, m), 2.40–2.20 (3H, m), 1.80–1.50 (6H, m). Analysis: Found C, 69.70; H, 7.15; N, 13.16; C$_{24}$H$_{28}$N$_4$O$_2$.0.5H$_2$O requires C, 69.71; H, 7.07; N, 13.09%. Rotation: [◊]$_D^{25}$=−40.9° (c=0.09, methanol).

EXAMPLE 2

(2S)-1-(1,3-Benzoxazol-2-yl)-N$^2$-[(3R)-1-benzylpyrrolidin-3-yl]-2-piperidinecarboxamide

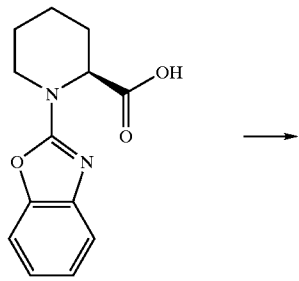

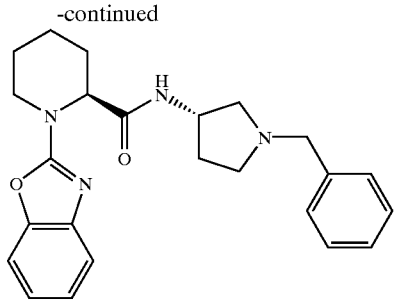

The title compound was prepared by a similar method to Example 1 from (2S)-1-(1,3-benzoxazol-2-yl)-2-piperidinecarboxylic acid [see Preparation 3] and (3S)-1-benzylpyrrolidin-3-ylamine. The crude product was purified by column chromatography on silica gel eluting with a solvent gradient of 50:50:1, changing to 20:80:1, by volume, hexane:ethyl acetate:0.88 aqueous ammonia solution, in 10% increments. The product was further purified by recrystallisation from ethyl acetate:hexane to afford (2S)-1-(1,3-benzoxazol-2-yl)-N$^2$-[(3S)-1-benzylpyrrolidin-3-yl]-2-piperidinecarboxamide as a white solid.

$^1$H-NMR (CDCl$_3$) δ: 7.40 (1H, d), 7.30 (1H, m), 7.20 (6H, s), 7.05 (1H, t), 6.60 (1H, d), 4.85 (1H, s), 4.45 (1H, bs), 4.25 (1H, d), 3.60 (2H, s), 3.20 (1H, t) 2.75 (1H, m), 2.55 (2H, m), 2.35 (1H, m), 2.25 (2H, m), 1.80–1.50 (4H, m), 1.30 (2H, m). Analysis: Found C, 71.00; H, 7.00; N, 13.80; C$_{24}$H$_{28}$N$_4$O$_2$ requires C, 71.26; H, 6.98; N, 13.85%. Rotation: [◊]$_D^{25}$=−102.0° (c=0.1, methanol).

EXAMPLE 3

(2S)-1-(1,3-Benzoxazol-2-yl)-N$^2$-[(3R)-pyrrolidin-3-yl]-2-piperidinecarboxamide

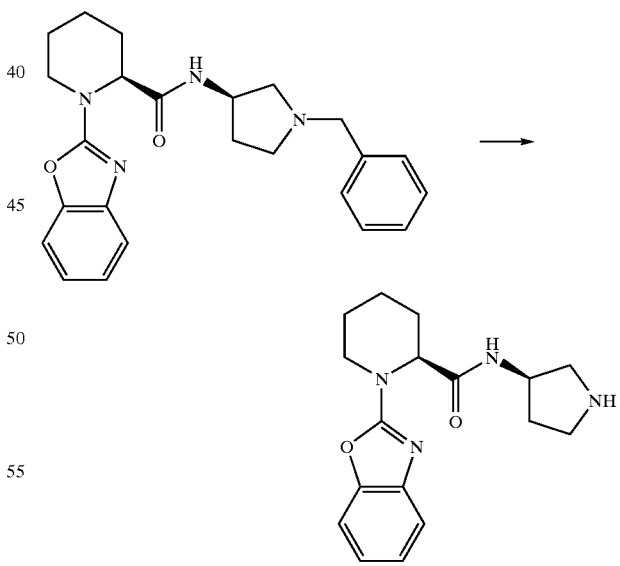

20% w/w Palladium hydroxide on carbon (12.5 mg) was added to a solution of (2S)-1-(1,3-benzoxazol-2-yl)-N$^2$-[(3R)-1-benzylpyrrolidin-3-yl]-2-piperidinecarboxamide (62.5 mg) [see Example 1] in ethanol (10 ml). The reaction mixture was hydrogenated at 414 kPa (60 p.s.i.) for 56 hours, after which time the catalyst was filtered off and the solvent removed under reduced pressure. The crude product was purified by column chromatography on silica gel eluting with a solvent gradient of 95:5 changing to 90:10, by volume, ethyl acetate:diethylamine to afford (2S)-1-(1,3-benzoxazol-2-yl)-N²-[(3R)-pyrrolidin-3-yl]-2-piperidinecarboxamide (1 mg) as an oil.

¹H-NMR (CDCl₃) δ: 7.35 (1H, d), 7.25 (1H, m), 7.20 (1H, t), 7.00 (1H, m), 6.65 (1H, bs), 4.85 (1H, bs), 4.40 (1H, bs), 4.25 (1H, d), 3.20 (1H, t), 2.80 (1H, bs), 2.65 (1H, m), 2.55 (1H, m), 2.40–2.20 (4H, m), 1.80–1.60 (6H, m). MS: 314 (MH⁺).

EXAMPLE 4

(2S)-1-(1,3-Benzoxazol-2-yl)-N²-[(3S)-pyrrolidin-3-yl]-2-piperidinecarboxamide

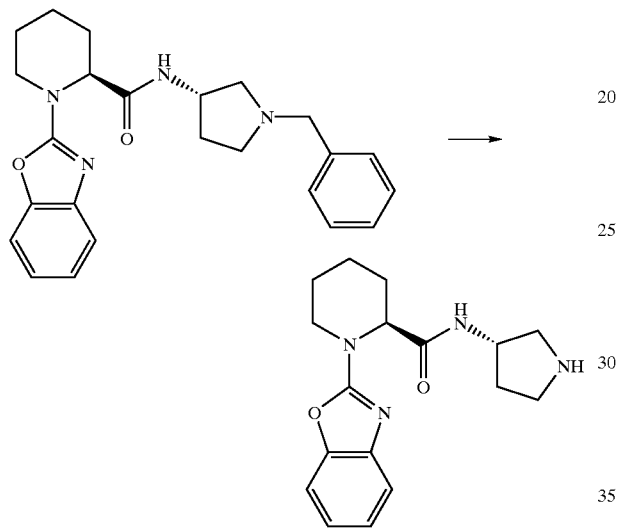

The title compound was prepared by a similar method to Example 3 from (2S)-1-(1,3-benzoxazol-2-yl)-N²-[(3S) benzylpyrrolidin-3-yl]-2-piperidinecarboxamide [see Example 2] and 20% palladium hydroxide on carbon to afford (2S)-1-(1,3-benzoxazol-2-yl)-N²-[(3S)-pyrrolidin-3-yl]-2-piperidinecarboxamide as a brown foam.

¹H-NMR (CDCl₃) δ: 7.30 (1H, d), 7.25 (1H, m), 7.20 (1H, m), 7.00 (1H, m), 6.60 (1H, d), 4.80 (1H, s), 4.40 (1H, m), 4.20 (1H, d), 3.25 (1H, t), 3.20 (1H, m), 3.00–2.80 (2H, m), 2.70 (1H, d), 2.40 (1H, m), 2.15 (1H, m), 1.80–1.50 (7H, m). Analysis: Found C, 60.85; H, 7.14; N, 15.79; C₁₇H₂₂N₄O₂·0.25 CH₂Cl₂ 0.4H₂O requires C, 60.43; H, 6.85; N, 16.34%.

EXAMPLE 5

(2S)-1-(1,3-Benzoxazol-2-yl)-N²-[(3S)-1-(2-pyridinyl)pyrrolidin-3-yl]-2-piperidinecarboxamide

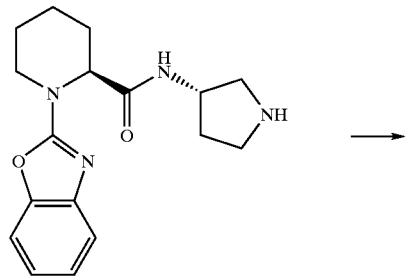

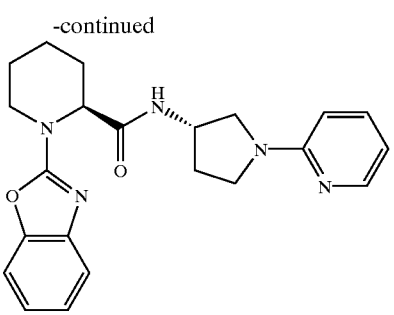

Sodium hydrogen carbonate (28.6 mg) was added to a solution of (2S)-1-(1,3-benzoxazol-2-yl)-N²-[(3S)-pyrrolidin-3-yl]-2-piperidinecarboxamide (104.9 mg) [see Example 4] and 2-bromopyridine (52.7 mg) in acetonitrile (5 ml). The reaction mixture was heated to 75° C. for 48 hours, after which time additional sodium hydrogen carbonate (28.6 mg) was added and the mixture was heated under reflux for a further 24 hours. The solvent was removed under reduced pressure and the residue was partitioned between ethyl acetate and water, the organic layer was separated, dried over magnesium sulphate and the solvent removed under reduced pressure. The crude product was purified by column chromatography on silica gel eluting with a solvent system of 93:7:1, by volume, dichloromethane:methanol:0.88 aqueous ammonia solution, and was then further purified by a second column eluting with 95:5, by volume, ethyl acetate:diethylamine to afford (2S)-1-(1,3-benzoxazol-2-yl)-N²-[(3S)-1-(2-pyridinyl)pyrrolidin-3-yl]-2-piperidinecarboxamide (11 mg) as a brown oil.

¹H-NMR (CDCl₃) δ: 8.15 (1H, d), 7.40 (1H, m), 7.25 (2H, m), 7.20 (1H, m), 7.05 (1H, m), 6.80 (1H, d), 6.60 (1H, t), 6.30 (1H, t), 4.90 (1H, m), 4.60 (1H, m), 4.25 (1H, d), 3.75 (1H, m), 3.50 (2H, m), 3.45 (1H, d), 3.20 (1H, t), 2.40–2.20 (2H, m), 2.05 (1H, m), 1.80–1.60 (5H, m). Accurate mass: Found 392.2073 (MH⁺), C₂₂H₂₅N₅O₂ requires 392.2086 (MH⁺).

EXAMPLE 6

(2S)-1-(1,3-Benzoxazol-2-yl)-N²-[(3S)-1-(2-pyridinylmethyl)pyrrolidin-3-yl]-2-piperidinecarboxamide

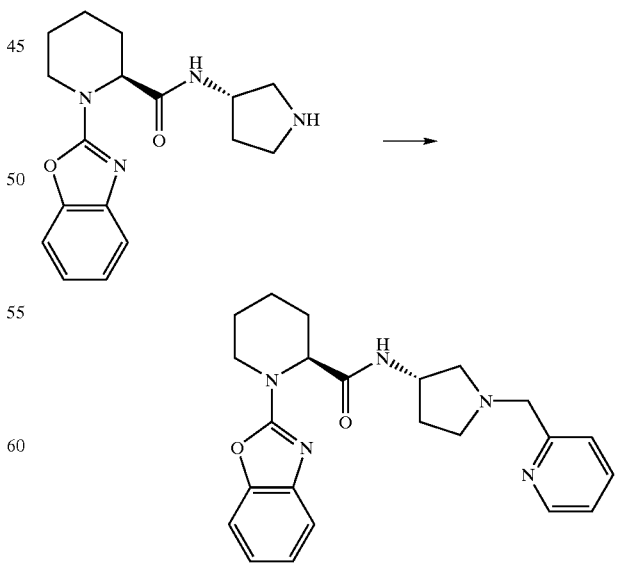

Potassium carbonate (0.052 g) was added to a solution of (2S)-1-(1,3-benzoxazol-2-yl)-N²-[(3S)-pyrrolidin-3-yl]-2- piperidinecarboxamide (108.2 mg) [see Example 4] and 2-(chloromethyl)pyridine in acetonitrile (6.8 ml, 0.055M) at 0° C. [2-(Chloromethyl)pyridine was prepared from 2-(chloromethyl)pyridine hydrochloride by partitioning between diethyl ether and saturated aqueous sodium hydrogen carbonate solution. The separated organic phase was washed with brine, dried over magnesium sulphate and the solvent removed under reduced pressure. The residual free base was immediately dissolved in acetonitrile and used]. The reaction mixture was stirred at room temperature for 18 hours, after which time the solvent was removed under reduced pressure and the residue partitioned between ethyl acetate and water. The organic layer was separated, dried over magnesium sulphate and the solvent removed under reduced pressure. The crude product was purified by column chromatography on silica gel eluting with a solvent system of 93:7:1, by volume, dichloromethane:methanol:0.88 aqueous ammonia solution to afford (2S)-1-(1,3-benzoxazol-2-yl)-$N^2$-[(3S)-1-(2-pyridinylmethyl)pyrrolidin-3-yl]-2-piperidinecarboxamide (63.1 mg) as an oil.

$^1$H-NMR (CDCl$_3$) δ: 8.45 (1H, d), 7.50 (1H, t), 7.40 (1H, d), 7.30–7.00 (5H, m), 6.80 (1H, d), 4.85 (1H, s), 4.50 (1H, m), 4.25 (1H, d), 3.70 (2H, t), 3.20 (1H, t), 2.80 (1H, m), 2.65 (1H, m), 2.55 (1H, d), 2.40–2.00 (4H, m), 1.80–1.60 (5H, m). Analysis: Found C, 62.01; H, 6.38; N, 15.39; C$_{23}$H$_{27}$N$_5$O$_2$. 1.25 H$_2$O. 0.25CH$_2$Cl$_2$ requires C, 62.16; H, 6.73; N, 15.59%.

EXAMPLES 7–9

The compounds of the following tabulated Examples (Table 1) of the general formula:

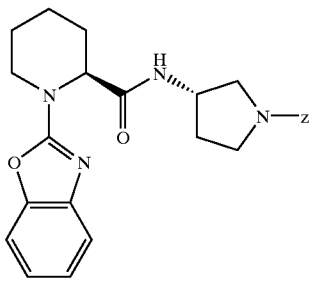

were prepared by a similar method to Example 6 from (2S)-1-(1,3-benzoxazol-2-yl)-$N^2$-[(3S)-pyrrolidin-3-yl]-2-piperidinecarboxamide [see Example 4] and the corresponding halide compound.

TABLE 1

| Example No. | Starting material Prep. No. | Z | Analytical data |
|---|---|---|---|
| 7[1] | 4 | 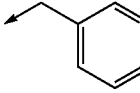 | $^1$H-NMR(DMSO-d$_6$)δ: 8.95(1H, s), 8.80(1H, d), 8.60(1H, d), 8.40(1H, d), 7.75(1H, s), 7.40(1H, d), 7.25(1H, d), 7.15(1H, t), 7.00(1H, t), 4.80(1H, m), 4.60–4.30(3H, m), 3.60(1H, m), 3.50(1H, m), 3.40–3.0(4H, m), 2.50–2.20(3H, m), 2.10–1.20(5H, m). Analysis: Found C, 51.42; H, 6.55; N, 12.51; C$_{23}$H$_{27}$N$_5$O$_2$.2HCl. 3.5H$_2$O. requires C, 51.02; H, 6.70; N, 12.93%. Rotation: $[◊]_D^{25}$ = –93.0° (c = 0.1, methanol). |
| 8 | 4 | 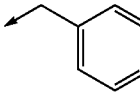 | $^1$H-NMR(CDCl$_3$)δ: 8.40(2H, d), 7.35 (1H, d), 7.25(1H, d), 7.20(1H, t), 7.10 (2H, m), 7.05(1H, m), 6.75(1H, d), 4.85(1H, s), 4.40(1H, m), 4.25(1H, d), 3.55(2H, s), 3.20(1H, t), 2.75(1H, m), 2.55(2H, m), 2.40(1H, m), 2.25 (3H, m), 1.80–1.50(5H, m). Analysis: Found C, 60.40; H, 6.16; N, 14.61; C$_{23}$H$_{27}$N$_5$O$_2$ 2H$_2$O. 0.25CH$_2$Cl$_2$ requires C, 60.34; H, 6.86; N, 15.13%. MS: 407(MH+). |
| 9 | 4 | 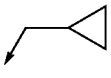 | $^1$H-NMR(CDCl$_3$)δ: 7.40(1H, d), 7.25 (1H, m), 7.20(1H, m), 7.05(1H, m), 6.70(1H, d), 4.90(1H, s), 4.45(1H, m), 4.25(1H, d), 3.20(1H, t), 2.80 (1H, t), 2.60(2H, d), 2.40(1H, m), 2.30(4H, m), 1.80–1.60(6H, m), 0.80 (1H, m), 0.45(2H, m), 0.00(2H, m). Analysis: Found C, 62.66; H, 7.30; N, 13.59; C$_{21}$H$_{28}$N$_4$O$_2$. 2H$_2$O requires C, 62.35; H, 7.97; N, 13.85%. MS: 369(MH+). Rotation: $[◊]_D^{25}$ = –90.0° (c = 0.1, methanol). |

Footnote
[1]Hydrochloride salt prepared by a similar method to that of Example 11.

EXAMPLE 10

(2S)-1-(1,3-Benzoxazol-2-yl)-N²-(3S)-1-[2-(2-pyridinyl)ethyl]pyrrolidin-3-yl-2-piperidinecarboxamide

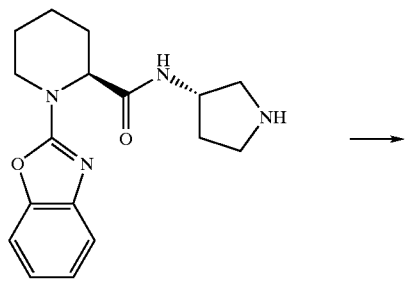

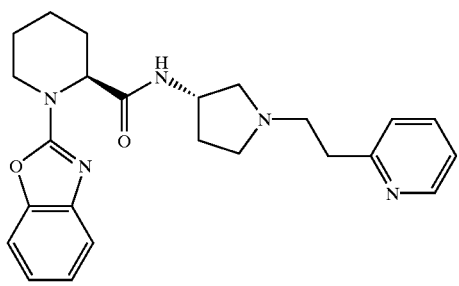

2-Vinylpyridine (0.02 ml) was added to a solution of (2S)-1-(1,3-benzoxazol-2-yl)-N²-[(3S)-pyrrolidin-3-yl]-2-piperidinecarboxamide (53.6 mg) [see Example 4] in diethyl ether (5 ml). Benzyltrimethyl ammonium hydroxide (40% w/w aqueous solution) (1 ml) was added and the reaction mixture stirred at reflux for 48 hours, after which time the solvent was removed under reduced pressure. The crude product was purified by column chromatography on silica gel eluting with 93:7:1, by volume, dichloromethane:methanol:0.88 aqueous ammonia solution, and the product was then further purified on a second column eluting with 95:5, by volume, ethyl acetate:diethylamine to afford (2S)-1-(1,3-benzoxazol-2-yl)-N²-(3S)-1-[2-(2-pyridinyl)ethyl]pyrrolidin-3-yl-2-piperidinecarboxamide (19.8 mg) as an oil.

$^1$H-NMR (CDCl$_3$) δ: 8.50 (1H, m), 7.60 (1H, m), 7.40 (1H, d), 7.25 (1H, m), 7.20–7.00 (4H, m), 6.65 (1H, bs), 4.90 (1H, s), 4.50 (1H, m), 4.25 (1H, d), 3.20 (1H, m), 3.00–2.80 (5H, m), 2.65 (2H, s), 2.40–2.20 (4H, m), 1.80–1.60 (5H, m). MS: 420 (MH$^+$).

EXAMPLE 11

(2S)-1-(1,3-Benzoxazol-2-yl)-N²-(3S)-1-[2-(2-methyl-1H-imdazol-1-yl)ethyl]pyrrolidin-3-yl-2-piperidinecarboxamide hydrochloride

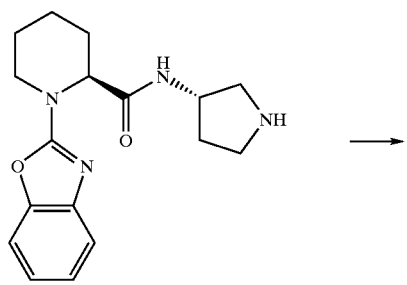

-continued

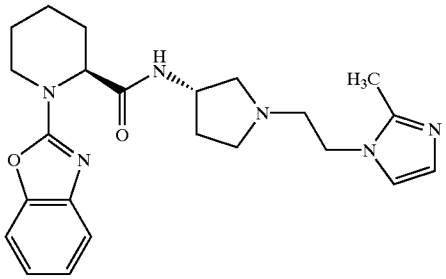

The title compound was prepared by a similar method to Example 5 from (2S)-1-(1,3-benzoxazol-2-yl)-N²-[(3S)-pyrrolidin-3-yl]-2-piperidinecarboxamide [see Example 4] and 1-(2-chloroethyl)-2-methyl-1H-imidazole [see U.S. Pat. No. 3,962,274, CAN 85: 177416]. The crude product was purified by column chromatography on silica gel eluting with a solvent system of 93:7:1, by volume, dichloromethane:methanol:0.88 aqueous ammonia solution to afford (2S)-1-(1,3-benzoxazol-2-yl)-N²-(3S)-1-[2-(2-methyl-1H-imidazol-1-yl)ethyl]pyrrolidin-3-yl-2-piperidinecarboxamide. The residual gum was dissolved in methanol and treated with a 1N solution of ethereal hydrogen chloride. The resulting suspension was evaporated and dried to give the product hydrochloride salt as a red coloured solid.

$^1$H-NMR (DMSO-d$_6$) δ: 8.55 (1H, m), 7.60 (1H, d), 7.50 (1H, d), 7.40 (1H, d), 7.25 (1H, m), 7.15 (1H, m), 7.00 (1H, m), 4.75 (1H, m), 4.45 (2H, t), 4.40 (1H, m), 4.00 (1H, m), 3.80–3.20 (7H, m), 2.70–2.25 (2H, m), 2.60 (3H, s), 2.20 (1H, d), 1.80–1.60 (3H, m), 1.50–1.10 (2H, m). Accurate Mass: Found 423.2516 (MH$^+$), C$_{23}$H$_{30}$N$_6$O$_2$ requires 423.2509 (MH$^+$).

EXAMPLE 12

(2S)-1-(1,3-Benzoxazol-2-yl)-N²-[(3S)-1-(1H-1,2,4-triazol-3-ylmethyl)pyrrolidin-3-yl]-2-piperidinecarboxamide

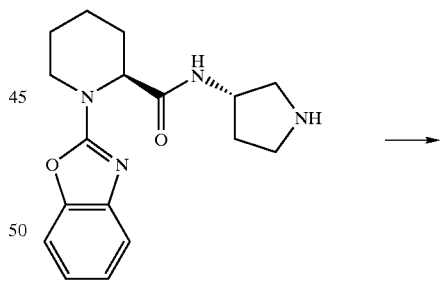

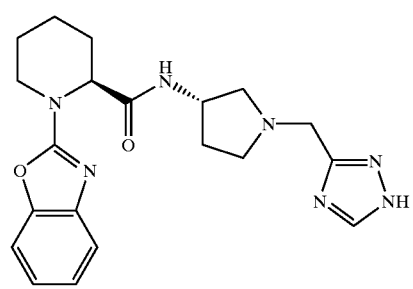

3-(Chloromethyl)-1H-1,2,4-triazole (70.8 mg) [see Bazhenov D. N. et al Zh. Org. Khim, (1994), 30(5), 791–792 and references cited therein] was added to a solution of (2S)-1-(1,3-benzoxazol-2-yl)-N$^2$-[(3S)pyrrolidin-3-yl]-2-piperidinecarboxamide (91.8 mg) [see Example 4], potassium carbonate (91 mg) and sodium iodide (10 mg) in acetonitrile (10 ml) at 0° C. The reaction mixture was stirred at room temperature for 18 hours, after which time the solvent was removed under reduced pressure and the residue partitioned between ethyl acetate and water. The organic layer was separated, dried over magnesium sulphate and the solvent removed under reduced pressure. The crude product was purified by column chromatography on silica gel eluting with a solvent system of 93:7:1, by volume, dichloromethane:methanol:0.88 aqueous ammonia solution to afford (2S)-1-(1,3-benzoxazol-2-yl)-N$^2$-[(3S)-1-(1H-1,2,4-triazol-3-ylmethyl)pyrrolidin-3-yl]-2-piperidinecarboxamide (12.6 mg) as a solid.

$^1$H-NMR (CDCl$_3$) δ: 8.00 (1H, s), 7.60 (1H, bs), 7.40 (1H, d), 7.25 (1H, m), 7.15 (1H, m), 7.00 (1H, m), 4.85 (1H, d), 4.45 (1H, d), 4.20 (1H, m), 3.95 (2H, m), 3.25 (1H, t), 3.00–2.20 (7H, m), 1.80–1.25 (5H, m). Accurate Mass: Found 396.2138 (MH$^+$), C$_{20}$H$_{25}$N$_7$O$_2$ requires 396.2148 (MH$^+$).

EXAMPLE 13

(2S)-N$^2$-[(3S)-1-((aminocarbonyl)methyl)pyrrolidin-3-yl]-1-(1, 3-benzoxazol-2-yl)-2-piperidinecarboxamide

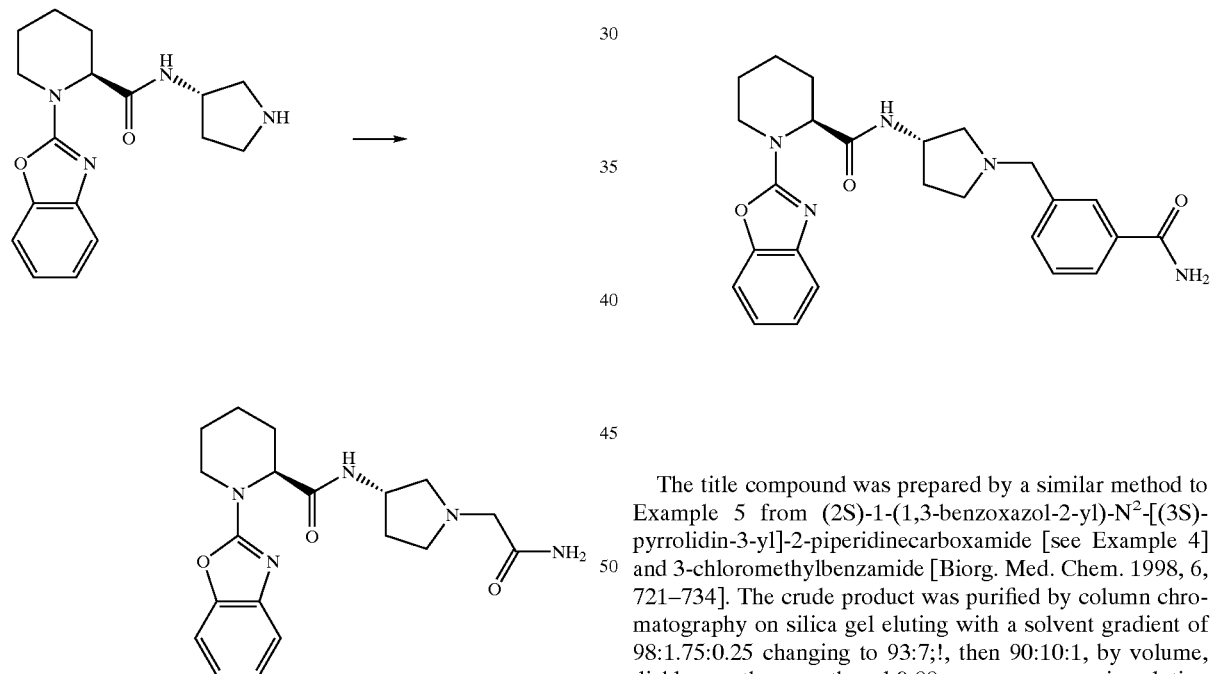

The title compound was prepared by a similar method to Example 5 from (2S)-1-(1,3-benzoxazol-2-yl)-N$^2$-[(3S)-pyrrolidin-3-yl]-2-piperidinecarboxamide [see Example 4] and 2-bromoacetamide. The crude product was purifies by column chromotography on silica gel eluting with a solvent gradient of 93:7:1, changing to 90:10:1, by volume, dichloromethane:methanol:0.88 aqueous ammonia solution to afford (2S)-N$^2$-[(3S)-1-((aminocarbonyl)methyl)pyrrolidin-3-yl]-1-(1,3-benzoxazol-2-yl)-2-piperidinecarboxamide as an oil.

$^1$H-NMR (CDCl$_3$) δ: 7.40 (1H, d), 7.30 (1H, m), 7.20 (1H, t), 7.10 (1H, t), 6.80 (1H, d), 6.60 (1H, bs), 5.20 (1H, bs), 4.85 (1H, s), 4.45 (1H, m), 4.25 (1H, d), 3.25 (1H, t), 3.10 (2H, s), 2.85 (1H, m), 2.75 (1H, m), 2.65 (1H, m), 2.50–2.20 (3H, m), 1.80–1.60 (6H, m). Accurate Mass: Found 372.2046 (MH$^+$), C$_{19}$H$_{25}$N$_5$O$_3$ requires 372.2036 (MH$^+$).

EXAMPLE 13A (2S)-N$^2$-{(3S)-1-[3-(Aminocarbonyl)phenylmethyl]pyrrolidin-3-yl}-1-(1, 3-benzoxazol-2-yl)-2-piperidinecarboxamide

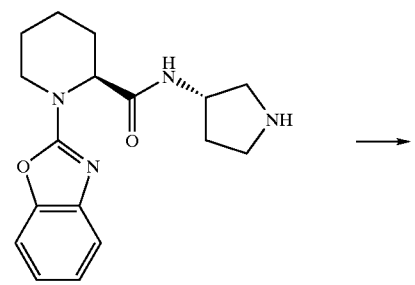

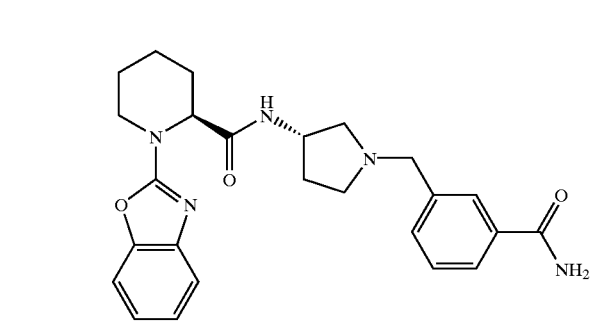

The title compound was prepared by a similar method to Example 5 from (2S)-1-(1,3-benzoxazol-2-yl)-N$^2$-[(3S)-pyrrolidin-3-yl]-2-piperidinecarboxamide [see Example 4] and 3-chloromethylbenzamide [Biorg. Med. Chem. 1998, 6, 721–734]. The crude product was purified by column chromatography on silica gel eluting with a solvent gradient of 98:1.75:0.25 changing to 93:7;!, then 90:10:1, by volume, dichloromethane:methanol:0.88 aqueous ammonia solution to afford (2S)-N$^2$-{(3S)-1-[3-(aminocarbonyl)methylphenyl]pyrrolidin-3-yl}-1-(1,3-benzoxazol-2-yl)-2-piperidinecarboxamide as an off-white solid.

NMR (CDCl$_3$) d: 7.80 (2H, m), 7.30 (4H, m), 7.20 (1H, m), 7.05 (1H, m), 6.70 (2H, bm), 5.50 (1H, bs), 4.85 (1H, s), 4.45 (1H, s), 4.25 (1H, d), 3.60 (2H, s), 3.20 (1H, t), 2.75 (1H, m), 2.50 (2H, m), 2.40 (1H, d), 2.25 (2H, m), 1.50–1.85 (6H, m). Analysis: Found C, 66.43, H, 6.51, N, 15.42, C$_{25}$H$_{29}$N$_5$O$_3$ 0.25H$_2$O requires C, 66.43, H, 6.58, N, 15.49%. MS: 448 (MH$^+$).

EXAMPLE 14

(2S)-N²-[(3S)-1-(aminocarbonylethyl)pyrrolidin-3-yl]-1-(1,3-benzoxazol-2-yl)-2-piperidinecarboxamide

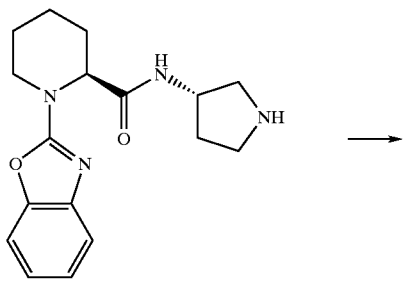

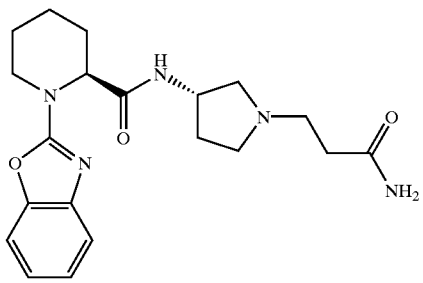

Acrylamide (11.6 mg) was added to a solution of (2S)-1-(1,3-benzoxazol-2-yl)-N²-[(3S)-pyrrolidin-3-yl]-2-piperidinecarboxamide (51.6 mg) [see Example 4] in diethyl ether (3 ml). The reaction mixture was refluxed for 18 hours, after which time the ethereal layer was diluted with water. The aqueous layer was separated and then extracted with ethyl acetate. The combined organic layers were dried over magnesium sulphate and the solvent removed under reduced pressure. The crude product was purified by column chromatography on silica gel eluting with a solvent gradient of 93:7:1, changing to 90:10:1, dichloromethane:methanol:0.88 aqueous ammonia solution to afford (2S)-N²-[(3S)-1-(aminocarbonylethyl)pyrrolidin-3-yl]-1-(1,3-benzoxazol-2-yl)-2-piperidinecarboxamide (26.4 mg) as an off-white foam.

¹H-NMR (CDCl₃) δ: 7.40 (1H, d), 7.30 (1H, m), 7.20 (1H, m), 7.10 (1H, t), 6.70 (1H, bs), 5.10 (1H, bs), 4.90 (1H, s), 4.45 (1H, m), 4.25 (1H, d), 3.20 (1H, t), 2.85 (1H, m), 2.75–2.60 (4H, m), 2.40–2.20 (5H, m), 1.80–1.55 (6H, m). MS: 386 (MH⁺).

EXAMPLE 15

(2S)-N²-[(3S)-1-Benzylpyrrolidin-3-yl]-1-(6-bromo-1,3-benzoxazol-2-yl)-2-piperidinecarboxamide

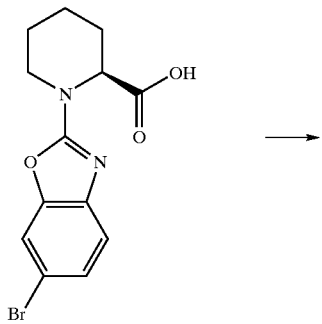

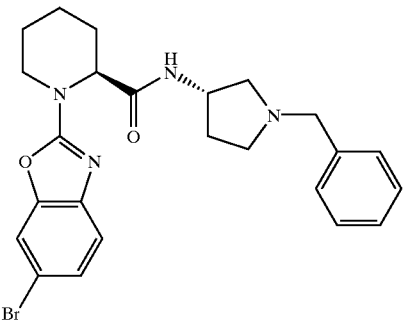

The title compound was prepared by a similar method to Example 1 from (2S)-1-(6-bromo-1,3-benzoxazol-2-yl)-2-piperidinecarboxylic [see Preparation 6] and (3R)-1-benzylpyrrolidin-3-ylamine. The crude product was purified by column chromatography on silica gel eluting with a solvent gradient of 50:50:1 changing to 40:60:1, by volume, hexane:ethyl acetate:triethylamine. The product was further purified by recrystallisation from isopropyl acetate to afford (2S)-N²-[(3S)-1-benzylpyrrolidin-3-yl]-1-(6-bromo-1,3-benzoxazol-2-yl)-2-piperidinecarboxamide as an oil.

¹H-NMR (CDCl₃) δ: 7.40 (1H, s), 7.30 (1H, d), 7.20 (6H, m), 6.60 (1H, d), 4.80 (1H, s), 4.40 (1H, bs), 4.20 (1H, d), 3.55 (2H, s), 3.20 (1H, t), 2.80 (1H, t), 2.55 (2H, m), 2.40–2.20 (3H, m), 1.80–1.50 (6H, m). Analysis: Found C, 59.54; H, 5.58; N, 11.54; C₂₄H₂₇N₄O₂Br requires C, 59.63; H, 5.63; N, 11.59%.

EXAMPLES 16 TO 20

The compounds of the following tabulated Examples (Table 2) of the general formula:

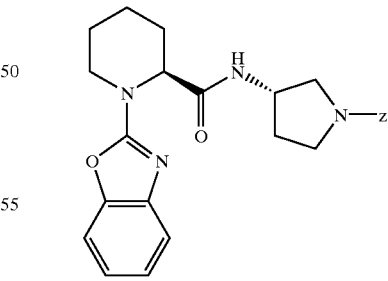

were prepared by a similar method to Example 1, with the exception that a catalytic amount of 4-diethylaminopyridine was also used in the amide coupling, from (2S)-1-(1,3-benzoxazol-2-yl)-2-piperidinecarboxylic acid [see Preparation 3] and the corresponding amine [see Preparations 8 and 13 to 16 (Table 2b)].

TABLE 2

| Example No. | Starting material Prep. No | Z | Analytical Data |
|---|---|---|---|
| 16 | 8 | 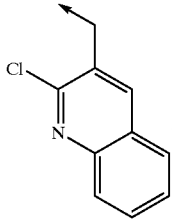 | ¹H-NMR(CDCl₃)δ: 8.09(1H, s), 7.96 (1H, d), 7.67(2H, m), 7.49(1H, m), 7.31(1H, d), 7.22(1H, m), 7.12(1H, m), 6.98(1H, m), 6.80(1H, bs), 4.88 (1H, s), 4.42(1H, bs), 4.25(1H, d), 3.80(2H, s), 3.20(1H, t), 2.95(1H, bs), 2.80–2.60(2H, m), 2.50–2.20(3H, m), 1.80–1.50(6H, m). MS: 490(MH⁺). R$_f$: 0.6(ethyl acetate). |
| 17 | 13 | 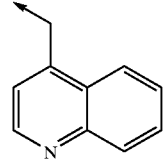 | ¹H-NMR(CDCl₃)δ: 8.70(1H, s), 8.10 (2H, m), 7.55(1H, m), 7.40–7.30(2H, m), 7.22(1H, m), 7.15(1H, m), 7.05 (1H, m), 6.77(1H, m), 4.85(1H, s), 4.42(1H, bs), 4.20(1H, d), 3.95(2H, s), 3.15(1H, m), 2.80(1H, m), 2.58 (2H, m), 2.40–2.20(3H, m), 1.80–1.40 (6H, m). MS: 456(MH⁺). R$_f$: 0.55(10:1, by volume, chloroform:methanol). |
| 18 | 14 | 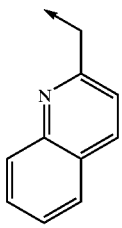 | ¹H-NMR(CDCl₃)δ: 8.00(1H, d), 7.85 (1H, d), 7.72(1H, d), 7.68(1H, m), 7.50(1H, m), 7.40(2H, m), 7.30(1H, m), 7.20(1H, m), 7.05(1H, m), 6.80 (1H, bs), 4.90(1H, s), 4.50(1H, bs), 4.22(1H, d), 3.90(2H, m), 3.20(1H, m), 2.90(1H, m), 2.60(2H, m), 2.42 (1H, m), 2.25(2H, m), 1.80–1.50(6H, m). MS: 456(MH⁺). R$_f$: 0.4(20:1, by volume, chloroform:methanol). |
| 19 | 15 | 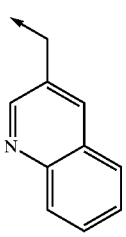 | ¹H-NMR(CDCl₃)δ: 8.80(1H, s), 8.10 (1H, d), 8.00(1H, s), 7.70(2H, m), 7.50(1H, m), 7.38(1H, d), 7.22(1H, m), 7.15(1H, m), 7.00(1H, m), 6.80 (1H, d), 4.82(1H, s), 4.50(1H, bs), 4.22(1H, d), 3.70(2H, m), 3.20(1H, m), 2.80(1H, m), 2.65(1H, m), 2.57 (1H, m), 2.40–2.20(3H, m), 1.80–1.40 (6H, m). MS: 456(MH⁺). R$_f$: 0.55(10:1, by volume, chloroform:methanol). |

TABLE 2-continued

| Example No. | Starting material Prep. No | Z | Analytical Data |
|---|---|---|---|
| 20 | 16 | ![quinoline with CH3] | ¹H-NMR(CDCl₃)δ: 8.80(1H, m), 8.30–8.15(1H, m), 8.10(1H, m), 7.70–7.50(1H, m), 7.50–7.10(4H, m), 7.00 (1H, m), 7.00–6.70(1H, m), 4.90(1H, m), 4.45(1H, m), 4.25(1H, m), 3.95 (1H, m), 3.20(1H, m), 3.10–2.70(1H, m), 2.65(1H, m), 2.60–2.10(4H, m), 1.80–1.40(6H, m), 1.40(3H, m). MS: 470(MH⁺). R_f: 0.4(20:1, by volume, chloroform:methanol). |

EXAMPLES 21 TO 26

The compounds of the following tabulated Examples (Table 3) of the general formula:

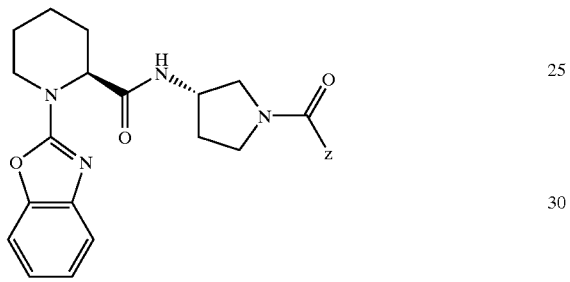

were prepared by a similar method to Example 1, excepting that a catalytic amount of 4-diethylaminopyridine was also used in the amide coupling, from (2S)-1-(1,3-benzoxazol-2-yl)-2-piperidinecarboxylic acid [see Preparation 3] and the corresponding amine [see Preparations 24 to 30 (Table 3b)].

TABLE 3

| Example No | Starting material Prep. No | Z | Analytical data |
|---|---|---|---|
| 21 | 24 | ![quinolin-2-yl] | ¹H-NMR(CDCl₃) (mixture of rotamers)δ: 8.22(1H, m), 8.10–7.50(5H, m), 7.40–7.00 (4H, m), 4.90(1H, m), 4.60 (1H, m), 4.42(1H, m), 4.20–3.05(5H, m), 2.30–1.80(2H, m), 1.80–1.40(6H, m). MS: 470(MH⁺). R_f: 0.4(20:1, by volume, chloroform:methanol). |
| 22 | 25 | ![2-phenylquinolin-4-yl] | ¹H-NMR(CDCl₃) (mixture of rotamers)δ: 8.20(3H, m), 7.80 (3H, m), 7.50(4H, m), 7.40–7.00(4H, m), 5.00–4.80(1H, ss), 4.65–4.35(1H, m), 4.35–4.00(2H, m), 4.00–3.40(2H, m), 3.40–3.00(2H, m), 2.40–2.00(2H, m), 2.00–1.40(6H, m). MS: 546(MH⁺). R_f: 0.62(20:1, by volume, chloroform:methanol) |

TABLE 3-continued

| Example No | Starting material Prep. No | Z | Analytical data |
|---|---|---|---|
| 23 | 26 | (4-methoxyquinolin-2-yl) | ¹H-NMR(CDCl₃) (mixture of rotamers)δ: 8.20(1H, m), 8.00 (1H, m), 7.80–7.40(2H, m), 7.40–6.90(5H, m), 4.90(1H, m), 4.70–4.40(1H, m), 4.30–3.60(5H, m), 4.10–4.05(3H, s), 3.40–3.10(1H, m), 2.40–2.10 (2H, m), 1.90(1H, m), 1.80–1.40(6H, m).<br>MS: 500(MH⁺).<br>R_f: 0.8(20:1, by volume, chloroform:methanol). |
| 24 | 27 | (6-methoxy-2-phenylquinolin-4-yl) | ¹H-NMR(CDCl₃) (mixture of rotamers)δ: 8.10(3H, m), 7.75 (1H, m), 7.5–7.20(4H, m), 7.20–7.00(5H, m), 4.90–4.70 (1H, bs), 4.70–4.30(1H, m), 4.30–4.00(2H, m), 3.90(3H, s), 3.80–3.50(2H, m), 3.30–3.00 (3H, m), 2.40–2.00(2H, m), 1.80–1.40(6H, m).<br>MS: 576(MH⁺).<br>R_f: 0.65(20:1, by volume, chloroform:methanol). |
| 25 | 28 | (2-piperidin-1-yl-quinolin-4-yl) | ¹H-NMR(CDCl₃) (mixture of rotamers)δ: 7.70(1H, bs), 7.55–7.40(2H, m), 7.40–6.95 (6H, m), 6.90(1H, s), 4.90–4.72 (1H, ss), 4.65–4.30(1H, m), 4.20(1H, m), 4.10–3.40(6H, m), 3.30–2.80(3H, m), 2.40–2.00(3H, m), 2.00–1.40(11H, m).<br>MS: 553(MH⁺).<br>R_f: 0.62(20:1, by volume, chloroform:methanol). |
| 26 | 29 | (2-chloroquinolin-4-yl) | ¹H-NMR(CDCl₃) (mixture of rotamers)δ: 8.05(1H, m), 7.75 (2H, m), 7.50(1H, m), 7.40–7.10(4H, m), 7.00(1H, m), 4.90–4.72(1H, ss), 4.55–4.35 (1H, mm), 4.20–2.80(6H, m), 2.40–2.00(2H, m), 2.00–1.40 (6H, m).<br>MS: 504(MH⁺).<br>R_f: 0.4(20:1, by volume, chloroform:methanol). |
| 27 | 30 | (1H-indazol-6-yl) | ¹H-NMR(CDCl₃) (mixture of rotamers)δ: 8.05(1H, s), 7.80–7.00(9H, m), 5.20–4.00(3H, m), 4.00–3.20(5H, m), 2.40–2.20(2H, m), 2.20–1.50(6H, m).<br>MS: 459(MH⁺).<br>R_f: 0.5(10:1, by volume, chloroform:methanol). |

EXAMPLE 28

(2S)-N[2]-(1-diphenylmethyl-3-azetidinyl)-1-(1,3-benzoxazol-2-yl)-2-piperidinecarboxamide

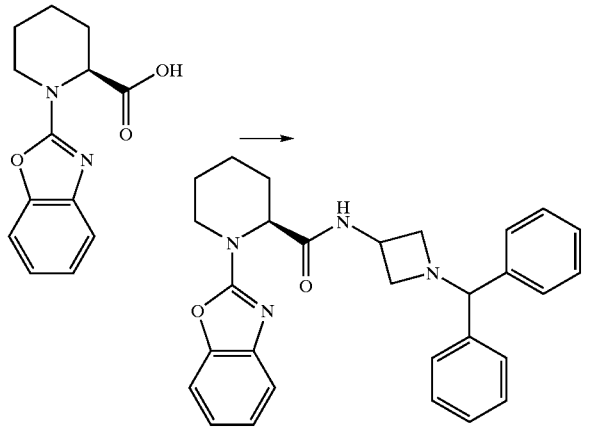

The title compound was prepared by a similar method to Example 1 from (2S)-1-(1,3-benzoxazol-2-yl)-2-piperidinecarboxylic acid [see Preparation 3] and 1-benzhydryl-3-azetanamine [see J. Med. Chem. (1977), 21(1), 78–82]. The crude product was purified by column chromatography on silica gel eluting with a solvent gradient of 80:20 changing to 60:40, then 50:50, by volume, hexane:ethyl acetate to afford (2S)-N[2]-(1-diphenylmethyl-3-azetidinyl)-1-(1,3-benzoxazol-2-yl)-2-piperidinecarboxamide as a white foam.

$^1$H-NMR (CDCl$_3$) δ: 7.40 (1H, d), 7.30 (5H, m), 7.20 (5H, m), 7.15 (2H, m), 7.10 (1H, t), 6.80 (1H, d), 4.90 (1H, s), 4.55 (1H, m), 4.25 (1H, s), 4.20 (1H, s), 3.50 (2H, t), 3.20 (1H, t), 2.85 (1H, m), 2.75 (1H, m), 2.35 (1H, m), 1.80–1.50 (5H, m). Analysis: Found C, 73.84; H, 6.48; N, 11.79, $C_{29}H_{30}N_4O_2 \cdot 0.33\ H_2O$ requires C, 73.71; H, 6.54; N, 11.86%.

EXAMPLE 29

(2S)-1-(1,3-Benzoxazol-2-yl)-N[2]-(1-ethyl-3-azetanyl)-2-piperidinecarboxamide

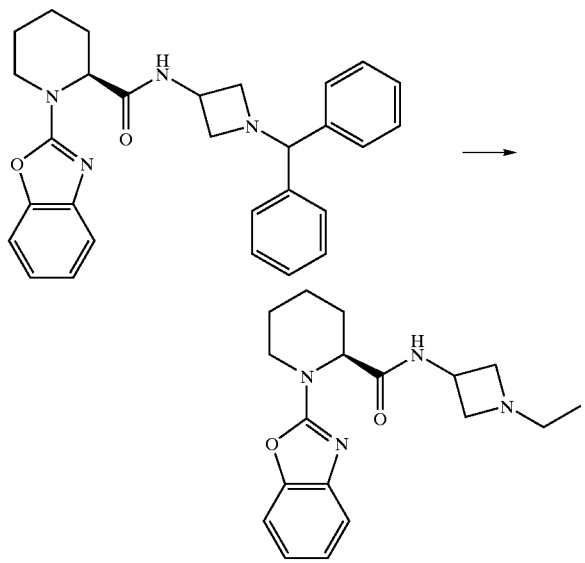

20% w/w Palladium hydroxide on carbon (31 mg) was added to a solution of (2S)-N[2]-(1-benzhydryl-3-azetanyl)-1-(1,3-benzoxazol-2-yl)-2-piperidinecarboxamide (120 mg) [see Example 28] in ethanol (5 ml). The reaction mixture was hydrogenated for 18 hours at 414 kPa (60 p.s.i.), after which time additional 20% w/w palladium hydroxide on carbon (32 mg) was added and the mixture hydrogenated for a further 72 hours. The catalyst was then filtered off and washed with ethanol and the solvent was removed under reduced pressure. The crude product was purified by column chromatography on silica gel eluting with a solvent gradient of 100:0 changing to 90:10, by volume, dichloromethane:methanol in 2% increments, to afford (2S)-1-(1,3-benzoxazol-2-yl)-N[2]-(1-ethyl-3-azetanyl)-2-piperidinecarboxamide (37.1 mg) as a foam.

$^1$H-NMR (CDCl$_3$) δ: 7.40 (1H, d), 7.30 (1H, m), 7.20 (1H, t), 7.05 (1H, t), 4.95 (1H, s), 4.60 (1H, m), 4.25 (1H, d), 3.75 (2H, t), 3.30–3.10 (3H, m), 2.60 (2H, q), 2.40 (1H, m), 1.80–1.60 (5H, m), 1.00 (3H, t). Analysis: Found C, 59.71; H, 7.17; N, 14.45; $C_{18}H_{24}N_4O_2 \cdot 0.55\ CH_2Cl_2$ requires C, 59.39; H, 6.74; N, 14.94%. MS: 329 (MH+).

EXAMPLE 30

(2S)-1-(1,3-Benzoxazol-2-yl)-N[2]-(1-benzyl-3-piperidinyl)-2-piperidinecarboxamide

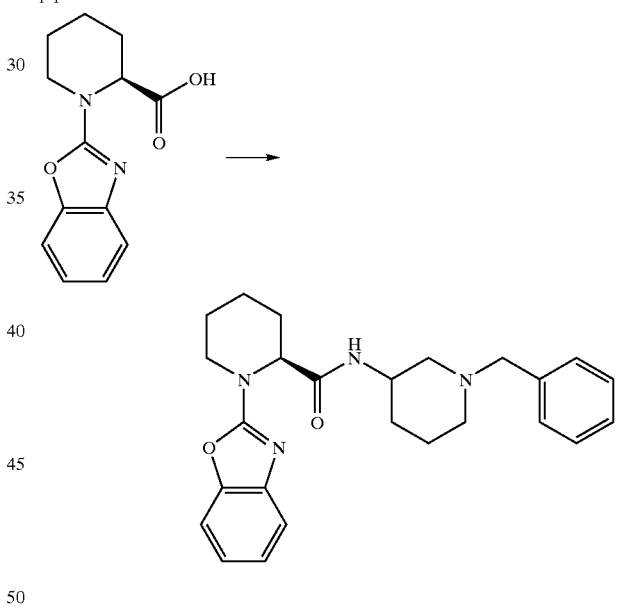

The title compound was prepared by a similar method to Example 1 from (2S)-1-(1,3-benzoxazol-2-yl)-2-piperidinecarboxylic acid [see Preparation 3] and 1-benzyl-3-piperidinylamine [see J. Med. Chem. (1980), 23(8), 848–851]. The crude product was purified by column chromatography on silica gel eluting with a solvent gradient of 90:10 changing to 40:60, by volume, hexane:ethyl acetate in 10% increments, to afford (2S)-1-(1,3-benzoxazol-2-yl)-N[2]-(1-benzyl-3-piperidinyl)hexahydro-2-pyridinecarboxamide as a yellow gum.

$^1$H-NMR (CDCl$_3$) δ: 7.40–7.00 (9H, m), 6.95 (1H, bs), 4.90 (1H, m), 4.30–4.20 (2H, 2xd), 4.10 (1H, m), 3.40 (1H, t), 3.25 (1H, t), 2.60 (1H, m), 2.40–2.20 (3H, m), 2.10 (1H, m), 1.90 (1H, m), 1.80–1.40 (8H, m). MS: 419 (MH+).

EXAMPLE 31

(2S)-1-(1,3-Benzoxazol-2-yl)-N²-(4-piperidinyl)-2-piperidinecarboxamide

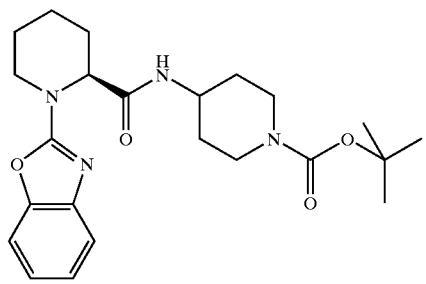

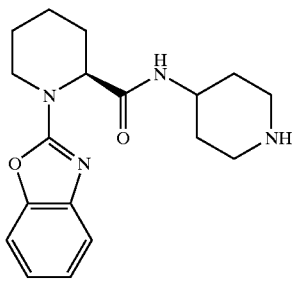

Trifluoroacetic acid (10 ml) was added to a solution of tert-butyl 4-([[(2S)-1-(1,3-benzoxazol-2-yl)-2-piperidinyl]carbonylamino)piperidine-1-carboxylate (1.631 g) [see Preparation 31] in dichloromethane (10 ml) at 0° C. The reaction mixture was then warmed to room temperature and stirred for 2 hours, after which time the solvent was removed under reduced pressure and the residue was dissolved in water. Sodium hydrogen carbonate was added until the solution reached a pH of 8 and the product was then extracted with ethyl acetate. The organic layer was separated, dried over magnesium sulphate and the solvent removed under reduced pressure to afford (2S)-1-(1,3-benzoxazol-2-yl)-N²-(4-piperidinyl)-2-piperidinecarboxamide (1.48 g) as a white foam.

¹H-NMR (CDCl₃) δ: 7.40 (1H, d), 7.30 (1H, m), 7.20 (1H, m), 7.10 (1H, t), 6.80 (1H, d), 4.85 (1H, s), 4.30 (1H, d), 4.00 (1H, m), 3.30 (2H, t), 3.20 (1H, t), 2.90 (2H, m), 2.35 (1H, d), 2.05 (2H, m), 1.80–1.60 (6H, m), 1.30 (2H, m). MS: 329 (MH⁺).

EXAMPLE 32

(2S)-1-(1,3-Benzoxazol-2-yl)-N²-(1-benzyl-4-piperidinyl)-2-piperidinecarboxamide

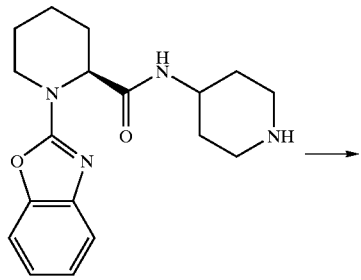

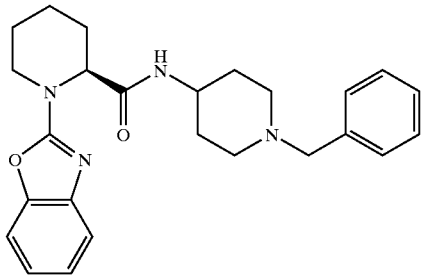

The title compound was prepared by a similar method to Example 6 from (2S)-1-(1,3-benzoxazol-2-yl)-N²-(4-piperidinyl)-2-piperidinecarboxamide [see Example 31] and benzyl bromide. The crude product was purified by column chromatography on silica gel eluting with a solvent system of 93:7:1, by volume, dichloromethane:methanol:0.88 aqueous ammonia solution to afford (2S)-1-(1,3-benzoxazol-2-yl)-N²-(1-benzyl-4-piperidinyl)-2-piperidinecarboxamide as an oil.

¹H-NMR (CDCl₃) δ: 7.40 (1H, d), 7.30–7.20 (7H, m), 7.10 (1H, t), 6.45 (1H, d), 4.90 (1H, s), 4.25 (1H, d), 3.85 (1H, m), 3.40 (2H, s), 3.20 (1H, t), 2.65 (2H, m), 2.40 (1H, d), 2.15 (2H, m), 1.90 (3H, m), 1.80–1.60 (4H, m), 1.30 (2H, m). Analysis: Found C, 69.87; H, 7.39; N, 12.79, $C_{25}H_{30}N_4O_2 \cdot 0.15 CH_2Cl_2$ requires C, 70.04; H, 7.08; N, 12.99%.

EXAMPLE 33

(2S)-1-(1,3-Benzoxazol-2-yl)-N²-[1-(4-pyridinylmethyl)-4-piperidinyl]-2-piperidinecarboxamide

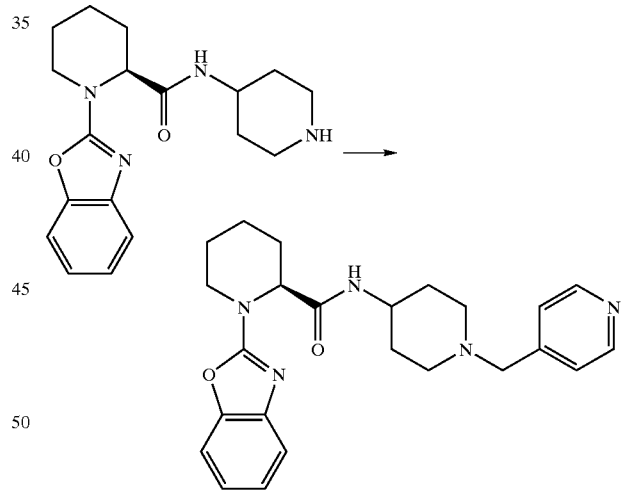

4-(Chloromethyl)pyridine (88.1 mg) was added to a solution of (2S)-1-(1,3-benzoxazol-2-yl)-N²-(4-piperidinyl)-2-piperidinecarboxamide (118 mg) [see Example 31], potassium carbonate (56.6 mg) and sodium iodide (6.7 mg) in acetonitrile (10 ml) at 0° C. The reaction mixture was then stirred at room temperature for 18 hours, after which time the solvent was removed under reduced pressure. The crude product was purified by column chromatography on silica gel eluting with a solvent system of 93:7:1, by volume, dichloromethane:methanol:0.88 aqueous ammonia solution to afford (2S)-1-(1,3-benzoxazol-2-yl)-N²-[1-(4-pyridinylmethyl)-4-piperidinyl]-2-piperidinecarboxamide (14.8 mg) as a red coloured gum.

¹H-NMR (CDCl₃) δ: 8.55 (2H, d), 7.40 (1H, m), 7.30 (2H, m), 7.25 (2H, m), 7.10 (1H, t), 6.50 (1H, d), 4.90 (1H, s), 4.25 (1H, d), 3.90 (1H, m), 3.40 (2H, s), 3.20 (1H, t), 2.75–2.60 (2H, m), 2.40 (1H, d), 2.20 (2H, m), 1.90 (2H, m), 1.80–1.60 (5H, m), 1.50 (2H, m). MS: 420 (MH+).

EXAMPLE 34 tert-Butyl (2S,4R)-4-([[(2S)-1-(1,3-benzoxazol-2-yl)-2-piperidinyl]carbonylamino)-2-[(benzyloxy)methyl]pyrrolidine-1-carboxylate

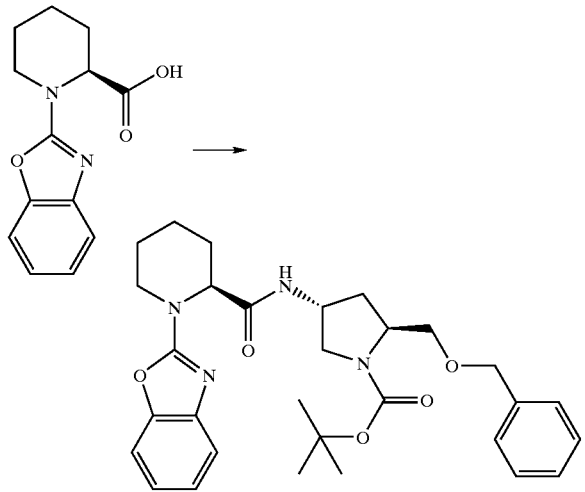

The title compound was prepared by a similar method to Example 1 from (2S)-1-(1,3-benzoxazol-2-yl)-2-piperidinecarboxylic acid [see Preparation 3] and tert-butyl (2S,4R)-4-amino-2-[(benzyloxy)methyl]pyrrolidine-1-carboxylate [see Preparation 34]. The crude product was purified by column chromatography on silica gel eluting with a solvent gradient of 70:30 changing to 50:50, by volume, hexane:ethyl acetate to afford tert-butyl (2S,4R)-4-([[(2S)-1-(1,3-benzoxazol-2-yl)-2-piperidinyl]carbonylamino)-2-[(benzyloxy)methyl]pyrrolidine-1-carboxylate as a foam.

¹H-NMR (CDCl₃) δ: 7.40–7.25 (7H, m), 7.20 (1H, t), 7.05 (1H, t), 6.55 (1H, d), 4.90 (1H, s), 4.55 (1, H m), 4.50 (2H, s), 4.25 (1H, d), 4.05–3.90 (1H, m), 3.65–3.50 (3H, m), 3.30–3.10 (2H, m), 2.35 (2H, m), 1.85–1.30 (14H, m), 0.90 (1H, m). Analysis: Found, C, 66.66; H, 7.22; N, 10.31; C₃₀H₃₈N₄O₅.0.25H₂O requires C, 66.83; H, 7.20; N, 10.39%. Rotation: $[◊]_D^{25}=-51.0°$ (c=0.1, methanol).

EXAMPLE 35

(2S)-1-(1,3-Benzoxazol-2-yl)-N²-(3R,5S)-5-[(benzyloxy)methyl]pyrrolidin-3-yl-2-piperidinecarbozamide hydrochloride

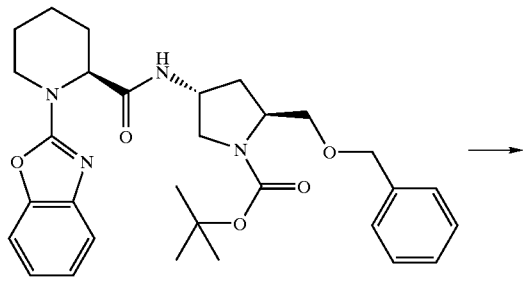

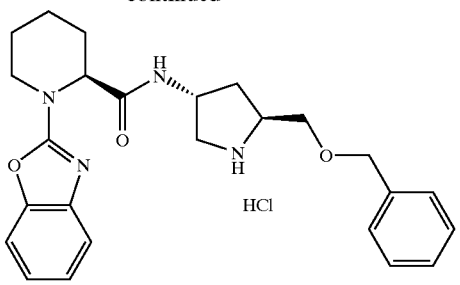

The title compound was prepared by a similar method to Preparation 8 from tert-butyl (2S,4R)-4-([[(2S)-1-(1,3-benzoxazol-2-yl)-2-piperidinyl]carbonylamino)-2-[(benzyloxy)methyl]pyrrolidine-1-carboxylate [see Example 34] and hydrogen chloride gas to afford (2S)-1-(1, 3-benzoxazol-2-yl)-N²-(3R,5S)-5-[(benzyloxy)methyl] pyrrolidin-3-yl-2-piperidinecarboxamide hydrochloride as a white solid.

¹H-NMR (DMSO-d₆) δ: 9.60 (1H, bs), 8.95 (1H, bs), 8.45 (1H, d), 7.40–7.25 (7H, m), 7.15 (1H, t), 7.00 (1H, t), 4.80 (1H, d), 4.55 (2H, s), 4.40 (1H, m), 4.15–4.05 (1H, m), 4.00 (1H, m), 3.70–3.60 (2H, m), 3.40 (2H, m), 3.10 (1H, m), 2.25 (1H, d), 2.00 (2H, m), 1.80–1.60 (3H, m), 1.55 (1H, m), 1.35 (1H, m). Analysis: Found C, 55.60; H, 6.39; N, 10.14; C₂₅H₃₀N₄O₃.2HCl.2H₂O requires C, 55.25; H, 6.67; N, 10.30%. Rotation: $[◊]_D^{25}=-19.0°$ (c=0.1, methanol).

EXAMPLE 36

(3S)-1-(2-Pyridinylmethyl)-3-piperidinyl (2S)-1-(1,3-benzoxazol-2-yl)-2-piperidinecarboxylate hydrochloride

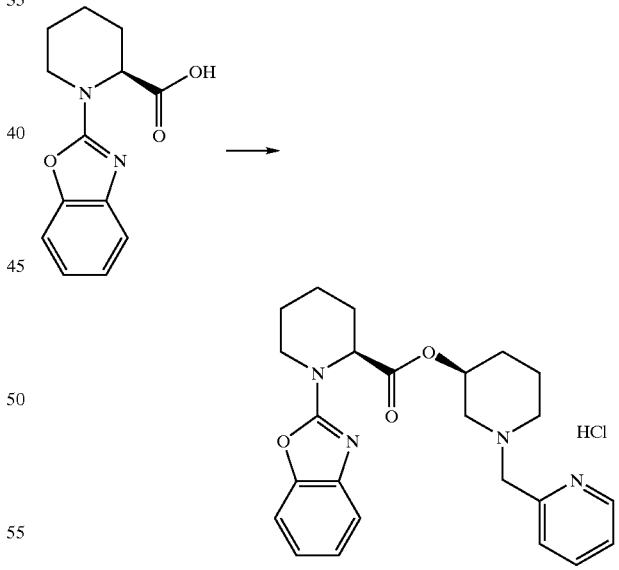

(3R)-1-(2-Pyridinylmethyl)-3-piperidinol (117 mg) [see Preparation 35] was added to a stirred solution of (2S)-1-(1,3-benzoxazol-2-yl)-2-piperidinecarboxylic acid (150 mg) [see Preparation 3], triphenylphosphine (192 mg) and diethyl azodicarboxylate (0.115 ml) in dry tetrahydrofuran (6 ml). The reaction mixture was stirred at reflux for 16 hours, after which time the solvent was removed under reduced pressure and the residue partitioned between ethyl acetate and 0.5M aqueous hydrochloric acid. The aqueous layer was then basified with 15% sodium hydroxide and the product extracted with ethyl acetate. The organic layer was then separated, dried over magnesium sulphate and the solvent removed under reduced pressure. The crude product was purified by column chromatography on silica gel eluting with 98:2, by volume, ethyl acetate:methanol to afford (3S)-1-(2-pyridinylmethyl)-3-piperidinyl (2S)-1-(1,3-benzoxazol-2-yl)-2-piperidinecarboxylate (140 mg) as a yellow oil. The hydrochloride salt was prepared by dissolving the title compound in ethyl acetate and bubbling hydrogen chloride gas through the solution, to afford the title compound as a white solid.

$^1$H-NMR (CDCl$_3$) (free base) δ: 8.30–8.20 (1H, m), 7.60–7.30 (1H, m), 7.20–7.15 (1H, m), 7.15–7.00 (2H, m), 7.00–6.90 (1H, m), 5.00–4.85 (2H, m), 4.20–4.00 (3H, m), 3.55 (1H, s), 3.50–3.45 (1H, d), 3.40–3.25 (1H, m), 2.90–2.75 (2H, m), 2.75–2.60 (1H, m), 2.50–2.40 (1H, m), 2.35–2.15 (2H, m), 1.90–1.40 (4H, m), 1.35–1.25 (1H, m), 1.25–1.10 (1H, m). MS: 421 (MH$^+$). Rotation: $[◊]_D^{25}$=−40.70° (c=1.0, methanol).

EXAMPLE 37

(3S,5S)-5-(Phenoxymethyl)-1-(4-pyridinylmethyl)pyrrolidin-3-yl (2 S)-1-(1,3-benzoxazol-2-yl)-2-piperidinecarboxylate hydrochloride

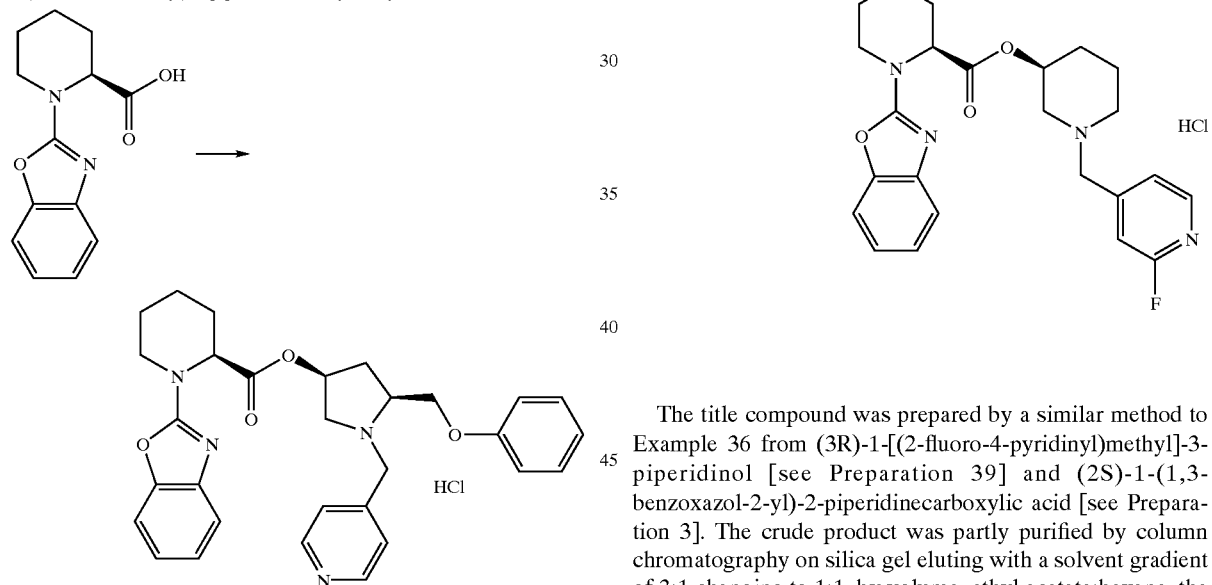

The title compound was prepared by a similar method to Example 36 from (3R,5S)-5-(phenoxymethyl)-1-(4-pyridinylmethyl)pyrrolidin-3-ol [see Preparation 38] and (2S)-1-(1,3-benzoxazol-2-yl)-2-piperidinecarboxylic acid [see Preparation 3]. The crude product was purified by column chromatography on silica gel eluting with a solvent gradient of 3:1 changing to 10:1, by volume, ethyl acetate-:hexane to afford the title compound. The hydrochloride salt was prepared by addition of saturated hydrogen chloride gas in diethyl ether to a solution of product in ethyl acetate, and isolated as a white solid.

$^1$H-NMR (CDCl$_3$) (free base) δ: 8.54–8.50 (1H, d), 8.39–8.37 (1H, d), 7.34–7.27 (1H, m), 7.26–7.18 (4H, m), 7.18–7.09 (2H, m), 7.02–6.95 (1H, m), 6.95–6.87 (1H, m), 6.84–6.80 (1H, d), 6.78–6.72 (1H, d), 5.08–5.00 (0.5H, m), 5.00–4.94 (1H, m), 4.70–4.64 (0.5H, m), 4.42–4.32 (1H, m), 4.30–4.20 (0.5H, m), 4.20–4.13 (1H, m), 4.10–4.02 (0.5H, d), 3.57 (1H, s), 3.38–3.28 (1H, m), 3.26–3.20 (0.5H, d), 3.11–3.05 (0.5H, d), 3.05–2.97 (1h, m), 2.92–2.83 (0.5H, m), 2.54–2.48 (0.5H, m), 2.46–2.41 (0.5H, dd), 2.39–2.31 (0.5H, m), 2.30–2.24 (1H, d), 2.16–2.06 (1H, m), 1.90–1.68 (3H, m), 1.64–1.50 (1H, m), 1.35–1.22 (2H,m). MS: 513 (MH$^+$). Rotation: $[◊]_D^{25}$=−18.00° (c=1.0, methanol).

EXAMPLE 38

(3S)-1-[(2-Fluoro-4-pyridinyl)methyl]-3-piperidinyl (2S)-1-(1,3-benzoxazol-2-yl)-2-piperidinecarboxylate hydrochloride

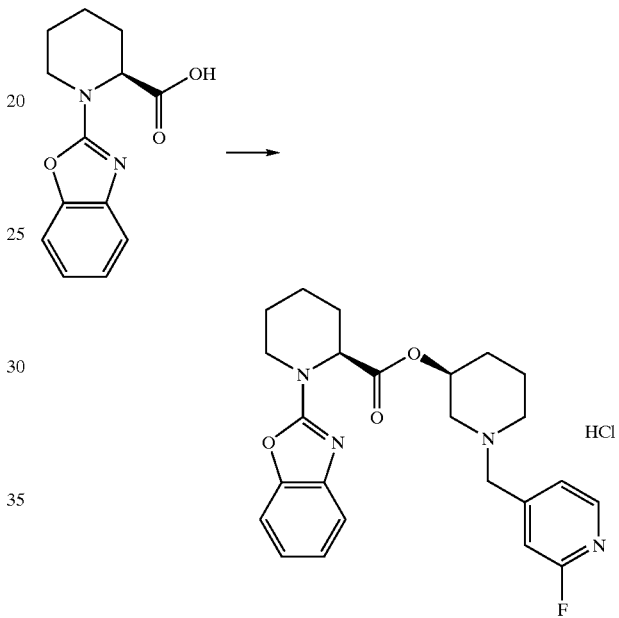

The title compound was prepared by a similar method to Example 36 from (3R)-1-[(2-fluoro-4-pyridinyl)methyl]-3-piperidinol [see Preparation 39] and (2S)-1-(1,3-benzoxazol-2-yl)-2-piperidinecarboxylic acid [see Preparation 3]. The crude product was partly purified by column chromatography on silica gel eluting with a solvent gradient of 3:1 changing to 1:1, by volume, ethyl acetate:hexane, the product was further purified by trituration with 95:5, by volume, hot hexane:ethyl acetate, followed by trituration with hot petroleum ether:diethyl ether, 95:5 to afford (3S)-1-[(2-fluoro-4-pyridinyl)methyl]-3-piperidinyl (2S)-1-(1,3-benzoxazol-2-yl)-2-piperidinecarboxylate. The hydrochloride salt was prepared by addition of saturated hydrogen chloride gas in diethyl ether to a solution of product in ethyl acetate, and isolated as a white solid.

$^1$H-NMR (CDCl$_3$) free base δ: 7.93–7.92 (1H, d), 7.29–6.85 (5H, m), 6.72 (1H, s), 5.00–4.80 (2H, m), 4.20–4.10 (2H, dd), 4.08–3.99 (1H, dd), 3.95–3.86 (1H, d), 3.35–3.21 (2H, m), 3.20–3.15 (1H, d), 2.79–2.65 (2H, m), 2.38–2.10 (2H, m), 2.10–1.95 (1H, dd), 1.90–1.60 (3H, m), 1.60–1.40 (2H, m), 1.40–1.20 (1H, m). MS: 439 (MH$^+$). Rotation: $[◊]_D^{25}$=−52.50° (c=1.0, methanol).

EXAMPLE 39

(2S)-1-(1,3-Benzothiazol-2-yl)-N-[(3S)-1-(3-pyridinylmethyl)pyrrolidin-3-yl]-2-piperidinecarboxamide

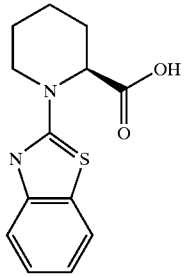

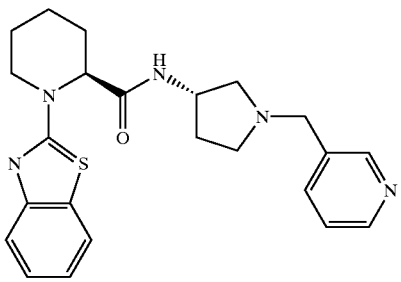

The title compound was prepared by a similar method to Example 1, excepting that a catalytic amount of 4-dimethylaminopyridine was also used, from (2S)-1-(1,3-benzothiazol-2-yl)-2-piperidinecarboxylic acid [see Preparation 43] and (3S)-1-(3-pyridinylmethyl)pyrrolidine-3-amine [see Preparation 41] to afford (2S)-1-(1,3-benzothiazol-2-yl)-N-[(3S)-1-(3-pyridinylmethyl)pyrrolidin-3-yl]-2-piperidinecarboxamide as a white solid.

$^1$H-NMR (CDCl$_3$) δ: 8.40 (1H, m), 7.60 (1H, m), 7.55–7.40 (2H, m), 7.22 (1H, m), 7.10 (2H, m), 6.80 (1H, m), 4.95 (1H, d), 4.40 (1H, bs), 3.80 (1H, m), 3.60–3.40 (2H, m), 3.25 (1H, m), 2.70 (1H, m), 2.60–2.30 (2H, m), 2.30–2.10 (3H, m), 1.80–1.40 (6H, m). MS: 422 (MH$^+$).

EXAMPLE 40

(2S)-N$^2$-[(3S)-1-Benzylpyrrolidin-3-yl]-1-(6-chloro-1,3-benzothiazol-2-yl)-2-piperidinecarboxamide

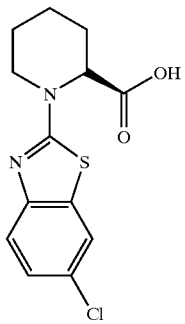

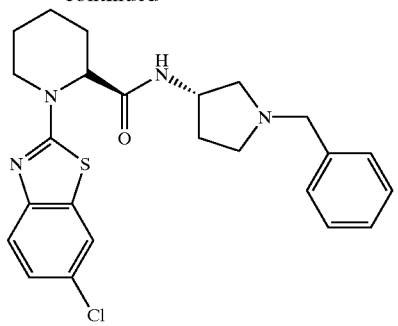

The title compound was prepared by a similar method to Example 1 from (2S)-1-(6-chloro-1,3-benzothiazol-2-yl)-2-piperidinecarboxylic acid [see Preparation 45] and (3S)-1-benzylpyrrolidin-3-ylamine [see J. Med. Chem. (1989), 31(8), 1586–1590] to afford (2S)-N$^2$-[(3S)-1-benzylpyrrolidin-3-yl]-1-(6-chloro-1,3-benzothiazol-2-yl)-2-piperidinecarboxamide as a solid.

$^1$H-NMR (CDCl$_3$) δ: 7.55 (1H, s), 7.40 (1H, m), 7.20 (5H, m), 6.75 (1H, m), 4.90 (1H, bs), 4.40 (1H, bs), 3.75 (1H, m), 3.60–3.20 (3H, m), 2.80 (1H, m), 2.55 (2H, m), 2.20 (2H, m), 1.80 (1H, m), 1.80–1.40 (6H, m). MS: 455 (MH$^+$).

EXAMPLE 41

1-(1H-1,3-Benzimidazol-2-yl)-N$^2$-[(3S)-1-benzylpyrrolidin-3-yl]-2-piperidinecarboxamide

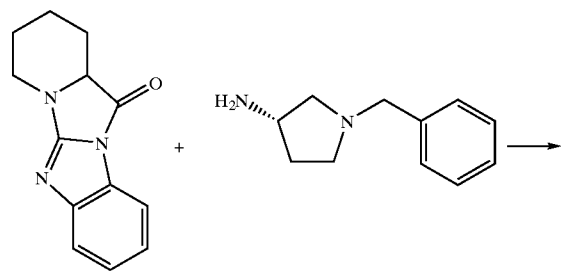

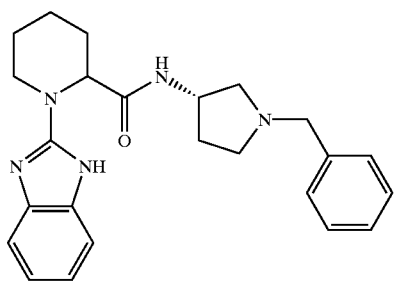

1,3,4,12a-Tetrahydropyrido[1',2':3,4]imidazo[1,2-a][1,3]benzimidazol-12(2H)-one (73 mg) [see Preparation 49] and (3S)-1-benzylpyrrolidin-3-ylamine (62 mg) were mixed in 1,4-dioxane (0.5 ml). The reaction mixture was heated to 90° C. and stirred for 4 hours, after which time the solvent was removed under reduced pressure and the residue was dissolved in dichloromethane:methanol and preabsorbed onto silica gel. The crude product was then purified by column chromatography on silica gel eluting with a solvent system of 99:1:0.1 to 97:3:0.3, by volume, dichloromethane:methanol:0.88 aqueous ammonia solution to afford 1-(1H-1,3-benzimidazol-2-yl)-N$^2$-[(3S)-1-benzyl-1-pyrrolidine-3-yl]-2-piperidinecarboxamide (69 mg) as a solid.

$^1$H-NMR (CDCl$_3$) δ: 8.90–8.70 (1H, d), 7.50–7.00 (9H, m), 4.80 (1H, d), 4.40 (1H, bs), 3.80 (2H, d), 3.60 (2H, d), 3.35 (1H, m), 2.75 (1H, m), 2.60–2.40 (2H, m), 2.20 (3H, m), 1.80–1.50 (5H, m). Analysis: Found C, 71.33, H, 7.33; N, 17.26, C$_{24}$H$_{29}$N$_5$O requires C, 71.44; H, 7.24; N, 17.36%. Rotation: $[◊]_D^{25}$=+6.00° (c=0.1, methanol).

The following Preparations illustrate the preparation of certain starting materials used in the preceding Examples.

Preparation 1
(2S)-2-(Methoxycarbonyl)piperidinium chloride

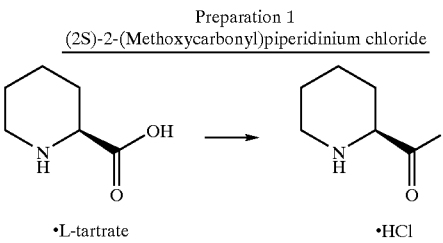

[(2S)-Piperidinecarboxylic acid L-tartrate (20.0 g) [see WO-A-96/11185] was added dropwise to a solution of thionyl chloride (54 ml) in methanol (270 ml) at 0° C. The reaction mixture was then stirred for 18 hours at room temperature, after which time the solvent was removed under reduced pressure and the residue was azeotroped with toluene (3×100 ml). The crude product was purified by recrystallisation from methanol (15 ml) with addition of diethyl ether to turbidity, affording (2S)-2-(methoxycarbonyl)piperidinium chloride (11.06 g) as white crystals.

$^1$H-NMR (D$_2$O) δ: 3.95 (1H, d), 3.70 (3H, m), 3.40 (1H, d), 3.00 (1H, t), 2.20 (1H, d), 1.80 (2H, m), 1.70–1.40 (3H, m). Rotation: $[◊]_D^{25}$=–8.40° (c=0.1, methanol). MS: 144 (MH$^+$).

Preparation 2
Methyl (2S)-1-(1,3-benzoxazol-2-yl)-2-piperidinecarboxylate

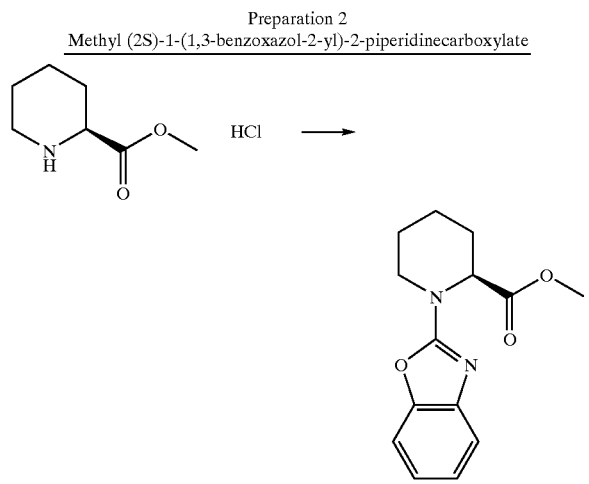

Ethyldiisopropylamine (6.52 ml) was added to a solution of (2S)-2-(methoxycarbonyl)piperidinium chloride (3.057 g) [see Preparation 1] and 2-chlorobenzoxazole (2.13 ml) in acetonitrile (50 ml). The reaction mixture was stirred at room temperature for 18 hours and then at 50° C. for a further 2 hours. The solvent was removed under reduced pressure and the residue partitioned between ethyl acetate and water, the organic layer was separated, dried over magnesium sulphate and the solvent removed under reduced pressure. The crude product was purified by column chromatography on silica gel eluting with a solvent gradient of 80:10:0, changing to 0:100:0, followed by 0:95:5, by volume, hexane:ethyl acetate:methanol, to afford methyl (2S)-1-(1,3-benzoxazol-2-yl)-2-piperidinecarboxylate (3.18 g) as a solid.

$^1$H-NMR (CDCl$_3$) δ: 7.35 (1H, d), 7.25 (1H, d), 7.15 (1H, m), 7.00 (1H, m), 5.00 (1H, d), 4.20 (1H, m), 3.70 (3H, s), 3.35 (1H, t), 2.30 (1H, d), 1.80 (3H, m), 1.60 (1H, m), 1.35 (1H, m). MS: 261 (MH$^+$).

Preparation 3
(2S)-1-(1,3-Benzoxazol-2-yl)-2-piperidinecarboxylic acid

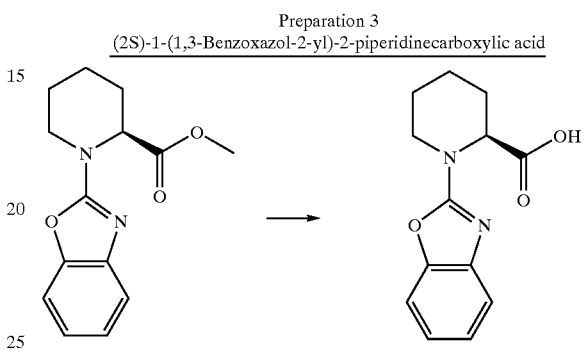

Aqueous lithium hydroxide (1N, 51 ml) was added to a solution of methyl (2S)-1-(1,3-benzoxazol-2-yl)-2-piperidinecarboxylate (8.987g) [see Preparation 2] in methanol (306 ml) at 0° C. The reaction mixture was stirred at room temperature for 18 hours, after which time the solvent was removed under reduced pressure and the residue partitioned between ethyl acetate and water. The aqueous layer was separated and acidified to pH 2 with 2N aqueous hydrochloric acid, the product was extracted with ethyl acetate, dried over magnesium sulphate and the solvent removed under reduced pressure to afford (2S)-1-(1,3-benzoxazol-2-yl)-2-piperidinecarboxylic acid (8.17 g) as a white solid.

$^1$H-NMR (CDCl$_3$) δ: 7.40 (1H, d), 7.25 (1H, m), 7.15 (1H, t), 7.00 (1H, t), 5.80 (1H, bs), 4.95 (1H, bs), 4.15 (1H, d), 3.40 (1H, t), 2.40 (1H, d), 1.80 (3H, m), 1.60–1.40 (2H, m). Rotation: $[◊]_D^{25}$=–116.2° (c=0.1, methanol); MS: 247 (MH$^+$).

Preparation 4
1-(Iodomethyl)cyclopropane

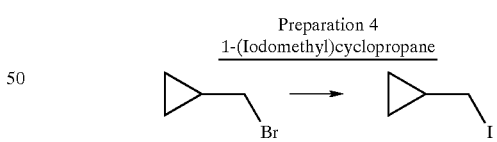

Sodium iodide (6.07 g) was added to a solution of 1-(bromomethyl)cyclopropane (1.09 g) in acetone (10 ml). The reaction mixture was heated to reflux and stirred for 18 hours, after which time the white solid was filtered off and the solvent removed under reduced pressure. The residue was partitioned between diethyl ether and water, and the separated organic layer was then washed with sodium thiosulphate, dried over magnesium sulphate and the solvent removed under reduced pressure to afford 1-(iodomethyl) cyclopropane (0.269 g) as a colourless liquid.

$^1$H-NMR (CDCl$_3$) δ: 3.15 (2H, d), 1.30 (1H, m), 0.80 (2H, m), 0.30 (2H, m).

Preparation 5
Methyl (2S)-1-(6-bromo-1,3-benzoxazol-2-yl)-2-piperidinecarboxylate

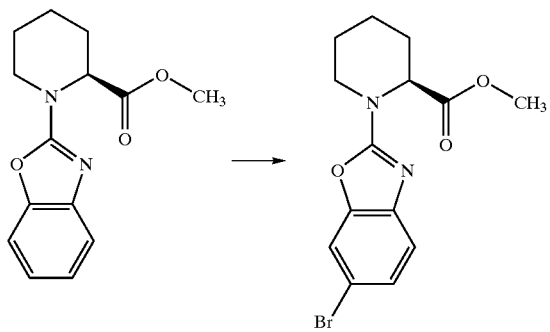

2,4,4,6-Tetrabromo-2,5-cyclohexadien-1-one (4.7 g) was added to a solution of methyl (2S)-1-(1,3-benzoxazol-2-yl)-2-piperidinecarboxylate (3.0 g) [see Preparation 2] in dichloromethane (60 ml) at −10° C. over a period of 10 minutes. The reaction mixture was then warmed to room temperature and diluted with dichloromethane. The organic layer was washed with saturated sodium hydrogen carbonate, then with 1N sodium hydroxide solution, dried over sodium sulphate and the solvent removed under reduced pressure to afford methyl (2S)-1-(6-bromo-1,3-benzoxazol-2-yl)-2-piperidinecarboxylate (3.7 g) as a purple coloured oil.

$^1$H-NMR (CDCl$_3$) δ: 7.40 (1H, s), 7.25 (1H, d), 7.20 (1H, d), 5.00 (1H, d), 4.20 (1H, d), 3.80 (3H, s), 3.40 (1H, t), 2.40 (1H, d), 1.80 (3H, m), 1.70 (2H,m), 1.40 (1H, m).

Preparation 6
(2S)-1-(6-Bromo-1,3-benzoxazol-2-yl)-2-piperidinecarboxylic acid

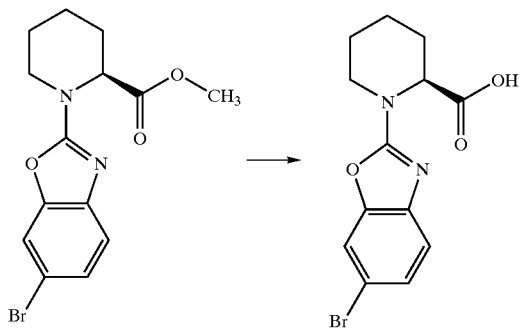

The title compound was prepared by a similar method to Preparation 3 from methyl (2S)-1-(6-bromo-1,3-benzoxazol-2-yl)-2-piperidinecarboxylate [see Preparation 5] and 1N aqueous lithium hydroxide solution, to afford (2S)-1-(6-bromo-1,3-benzoxazol-2-yl)-2-piperidinecarboxylic acid as a pink foam.

$^1$H-NMR (CDCl$_3$) δ: 7.40 (1H, s), 7.25–7.20 (2H, m), 5.00 (1H, d), 4.80 (1H, bs), 4.20 (1H, d), 3.40 (1H, t), 2.40 (1H, d), 1.90 (3H, m), 1.70–1.40 (2H, m). MS: 325 (MH+).

Preparation 7
tert-Butyl N-(3S)-1-[(2-chloro-3-quinolinyl)methyl]pyrrolidin-3-ylcarbamate

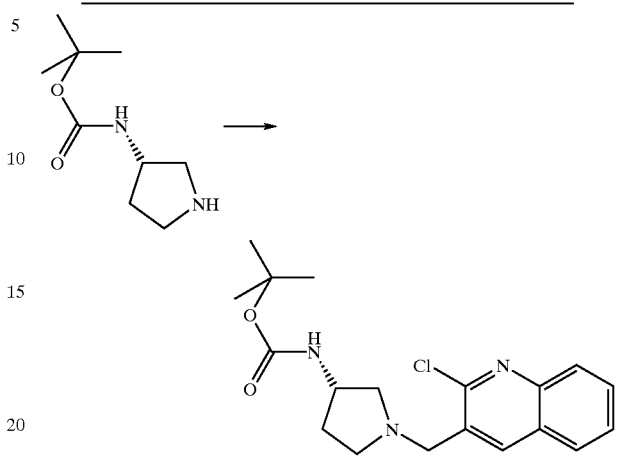

Sodium triacetoxyborohydride (2.3 g) was added to a solution of tert-butyl N-[(3S)-pyrrolidin-3-yl]carbamate (1.0 g) [see J. Het. Chem. (1990), 27, 1527–1536] and 2-chloro-3-quinolinecarbaldehyde (1.1 g) [see Ind. J. Chem. Soc. (1985), 24, 1286–1287] in dichloromethane (20 ml). The reaction mixture was stirred at room temperature for 18 hours, after which time water (20 ml) was added and the mixture stirred for a further 1 hour. The organic layer was then separated, washed with saturated aqueous sodium hydrogen carbonate solution, dried over magnesium sulphate and the solvent removed under reduced pressure. The crude product was purified by column chromatography on silica gel eluting with a solvent system of 1:1, by volume, ethyl acetate:chloroform to afford tert-butyl N-(3S)-1-[(2-chloro-3-quinolinyl)methyl]-1-pyrrolidine-3-ylcarbamate (1.6 g) as an oil.

$^1$H-NMR (CDCl$_3$) δ: 8.20 (1H, s), 7.98 (1H, d), 7.80 (1H, d), 7.68 (1H, m), 7.55 (1H, m), 5.85 (1H, bs), 4.22 (1H, bs), 3.82 (2H, s), 2.85 (1H, bs), 2.78 (1H, m), 2.65 (1H, m), 2.50 (1H, m), 2.28 (1H, m), 1.65 (1H, m), 1.40 (9H, s). MS: 262 (MH+).

Preparation 8
(3S)-1-[(2-Chloro-3-quinolinyl)methyl]pyrrolidine-3-amine hydrochloride

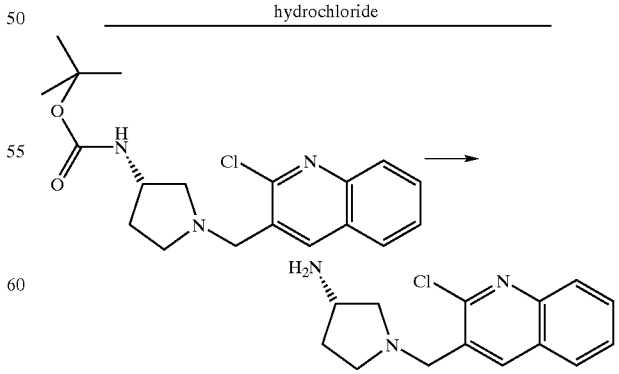

Hydrogen chloride gas was bubbled through a solution of tert-butyl N-(3S)-1-[(2-chloro-3-quinolinyl)methyl]

pyrrolidin-3-ylcarbamate (1.6 g) [see Preparation 7] in chloroform (20 ml) until a point of saturation. The reaction mixture was stirred at room temperature for 18 hours, after which time the solvent was removed under reduced pressure to afford (3S)-1-[(2-chloro-3-quinolinyl)methyl]pyrrolidin-3-amine hydrochloride (1.5 g) as a white solid.

MS: 262 (MH$^+$). R$_f$: 0.1 (10:1, by volume, ethyl acetate:chloroform).

PREPARATIONS 9 TO 12

The compounds of the following tabulated Preparations (Table 2a) of the general formula:

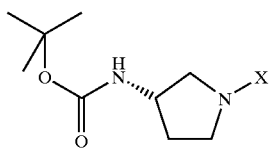

were prepared by a similar method to Preparation 7 from tert-butyl N[(3S)-pyrrolidin-3-yl]carbamate [see J. Het. Chem. (1990), 27, 1527–1536] and the corresponding aldehyde or ketone.

TABLE 2a

| Preparation No. | X | Analytical Data |
|---|---|---|
| 9 | 4-quinolinylmethyl | $^1$H-NMR(CDCl$_3$)δ: 8.82(1H, s), 8.15(1H, d), 8.10(1H, d), 7.65(1H, t), 7.52(1H, t), 7.40(1H, d), 4.90(1H, m), 4.20(1H, bs), 4.00(2H, s), 2.80(1H, m), 2.65(1H, m), 2.58(1H, m), 2.40(1H, m), 2.23(1H, m), 1.60(1H, m), 1.40(9H, s). MS: 328(MH$^+$). R$_f$ 0.6(10:1, by volume, ethyl acetate:chloroform). |
| 10 | 2-quinolinylmethyl | $^1$H-NMR(CDCl$_3$)δ: 8.10(2H, m), 7.80 (1H, m), 7.65(1H, m), 7.50(2H, m), 5.00 (1H, bs), 4.20(1H, bs), 3.90(2H, s), 2.85 (1H, m), 2.75(1H, m), 2.60(1H, m), 2.45 (1H, m), 2.22(1H, m), 1.60(1H, m), 1.38 (9H, s). MS: 328(MH$^+$). R$_f$: 0.6(10:1, by volume, ethyl acetate: chloroform). |
| 11 | 3-quinolinylmethyl | $^1$H-NMR(CDCl$_3$)δ: 8.85(1H, s), 8.10(2H, m), 7.80(1H, m), 7.70(1H, m), 7.50(1H, m), 4.90(1H, bs), 4.18(1H, bs), 3.75(2H, s), 2.80(1H, bs), 2.60(2H, m), 2.40–2.20(2H, m), 1.60(1H, m), 1.40(9H, s). MS: 328(MH$^+$). R$_f$: 0.6(10:1, by volume, ethyl acetate: chloroform). |
| 12 | 1-(4-quinolinyl)ethyl (Synthesis, 1984, 3, 245)[1] | MS: 342(MH$^+$). R$_f$: 0.5(10:1, by volume, chloroform: methanol). |

Footnote
[1] Starting material preparation.

PREPARATIONS 13 TO 16

The compounds of the following tabulated Preparations (Table 2b) were prepared by a similar method to Preparation 8 from the corresponding t-butyl carbamate [see Table 2a].

TABLE 2b

| Preparation No. | Starting material Prep. No. | Product | Analytical Data |
|---|---|---|---|
| 13 | 9 | (3S)-1-(4-quinolinylmethyl)pyrrolidin-3-amine | MS: 229 (MH$^+$). |
| 14 | 10 | (3S)-1-(2-quinolinylmethyl)pyrrolidin-3-amine | MS: 228 (MH$^+$). |
| 15 | 11 | (3S)-1-(3-quinolinylmethyl)pyrrolidin-3-amine | MS: 228 (MH$^+$). R$_f$: 0.1 (10:1, by volume, ethyl acetate: chloroform). |

TABLE 2b-continued

| Preparation No. | Starting material Prep. No. | Product | Analytical Data |
|---|---|---|---|
| 16 | 12 | 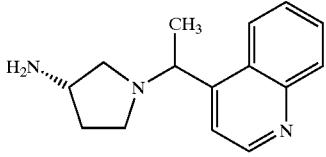 | MS: 242 (MH$^+$). $R_f$: 0.1 (10:1, by volume, chloroform:methanol). |

PREPARATION 17 TO 23

The compounds of the following tabulated Preparations (Table 3a) of the general formula:

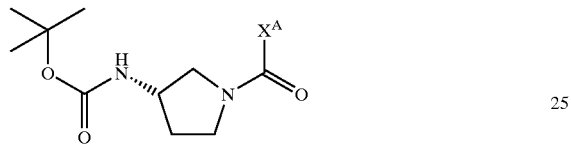

were prepared by a similar method to Example 1 from tert-butyl N-[(3S)-pyrrolidin-3-yl]carbamate [see J. Het. Chem. (1990), 27, 1527–1536] and the corresponding carboxylic acid.

TABLE 3a

| Preparation No. | X$^A$ | Analytical Data |
|---|---|---|
| 17 | 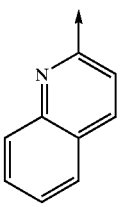 | $^1$H-NMR (CDCl$_3$) δ: 8.22 (1H, d), 8.05 (1H, d), 7.95 (1H, m), 7.82 (1H, d), 7.75 (1H, m), 7.60 (1H, m), 4.80 (1H, bs), 4.20–3.90 (3H, m), 3.80 (2H, m), 2.20 (1H, m), 1.90 (1H, m), 1.40 (9H, s). MS: 342 (MH$^+$). |
| 18 | 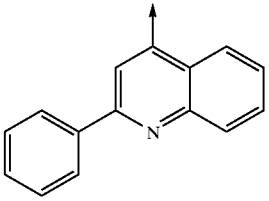<br>(J. Am. Chem. Soc., 1932, 54, 4732)[1]. | $^1$H-NMR (mixture of rotamers) (CDCl$_3$) δ: 8.20 (1H, m), 8.10 (2H, m), 7.70 (3H, m), 7.50 (4H, m), 4.50–3.00 (6H, m), 2.40–1.80 (2H, m), 1.45–1.25 (9H, s). MS: 418 (MH$^+$). $R_f$: 0.70 (20:1, by volume, chloroform:methanol). |
| 19 | 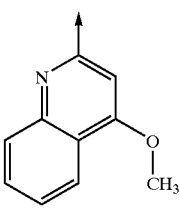 | $^1$H-NMR (mixture of rotamers) (CDCl$_3$) δ: 8.20 (1H, m), 8.00 (1H, m), 7.70 (1H, m), 7.52 (1H, m), 7.30 (1H, m), 4.80 (1H, bs), 4.05 (3H, s), 4.40–2.60 (5H, m), 2.20 (1H, m), 1.90 (1H, m), 1.42–1.40 (9H, ss). MS: 371 (MH$^+$). $R_f$: 0.8 (20:1, by volume, chloroform:methanol). |

TABLE 3a-continued

| Preparation No. | X^A | Analytical Data |
|---|---|---|
| 20 | 2-phenyl-6-methoxy-quinolin-4-yl | ¹H-NMR (mixture of rotamers) (CDCl₃) δ: 8.05 (3H, m), 7.78 (1H, d), 7.50–7.30 (4H, m), 7.00 (1H, m), 4.82–4.65 (1H, bsbs), 4.30–4.10 (1H, bsbs), 3.82 (3H, s), 4.10–3.60 (2H, m), 3.50–3.00 (2H, m), 2.40–1.80 (2H, m), 1.40–1.20 (9H, ss). MS: 448 (MH⁺). $R_f$: 0.75 (10:1, by volume, chloroform: methanol). |
| 21 | 2-piperidin-1-yl-[1,8]naphthyridin-4-yl | ¹H-NMR (mixture of rotamers) (CDCl₃) δ: 7.70 (1H, bs), 7.50 (2H, m), 7.19 (1H, m), 6.90 (1H, d), 4.75–4.55 (1H, m), 4.40–3.80 (2H, m), 3.80–3.60 (3H, m), 3.60–2.90 (3H, m), 2.30–1.70 (2H, m), 1.75–1.55 (6H, m), 1.42–1.35 (9H, ss). MS: 325 (MH⁺). $R_f$: 0.4 (10:1, by volume, chloroform: methanol). |
| 22 | 2-chloro-quinolin-4-yl | MS: 376 (MH⁺). $R_f$: 0.8 (10:1, by volume, chloroform: methanol). |
| 23 | 1H-indazol-6-yl (Helv. Chim. Acta, 1976, 59, 2618)[1]. | ¹H-NMR (mixture of rotamers) (CDCl₃) δ: 8.00 (1H, s), 7.65 (1H, d), 7.50 (1H, m), 7.18 (1H, m), 5.40–5.20 (1H, bsbs), 4.30–4.10 (1H, bsbs), 3.90–3.10 (5H, m), 2.30–1.80 (2H, m), 1.42–1.30 (9H, ss). MS: 331.2 (MH⁺). |

Footnote
[1] Starting material preparation.

PREPARATIONS 24 TO 30

The compounds of the following tabulated Preparations (Table 3b) were prepared by a similar method to Preparation 8 from the corresponding t-butyl carbamate [see Table 3a].

TABLE 3b

| Preparation No. | Starting material Prep. No. | Product | Analytical Data |
|---|---|---|---|
| 24 | 17 | 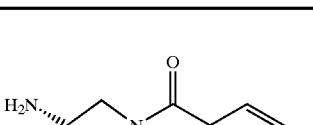 | MS: 242 (MH⁺). $R_f$: 0.1 (10:1, by volume, chloroform: methanol). |

TABLE 3b-continued
| Preparation No. | Starting material Prep. No. | Product | Analytical Data |
|---|---|---|---|
| 25 | 18 | 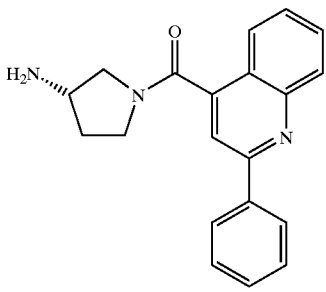 | MS: 318 (MH+). Rf: 0.1 (20:1, by volume, chloroform: methanol). |
| 26 | 19 | 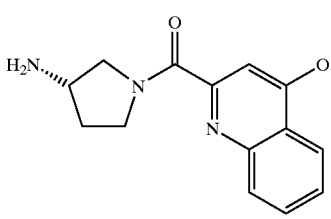 | MS: 272 (MH+). Rf: 0.15 (20:1, by volume, chloroform: methanol). |
| 27 | 20 | 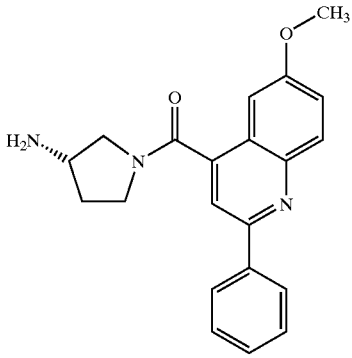 | MS: 348 (MH+). Rf: 0.1 (10:1, by volume, chloroform: methanol). |
| 28 | 21 | 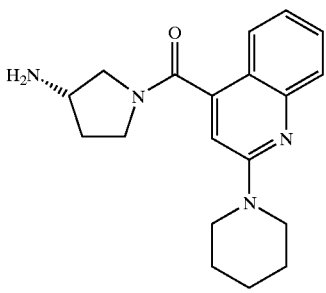 | MS: 325 (MH+). Rf: 0.1 (10:1, by volume, chloroform: methanol). |

TABLE 3b-continued

| Preparation No. | Starting material Prep. No. | Product | Analytical Data |
|---|---|---|---|
| 29 | 22 | 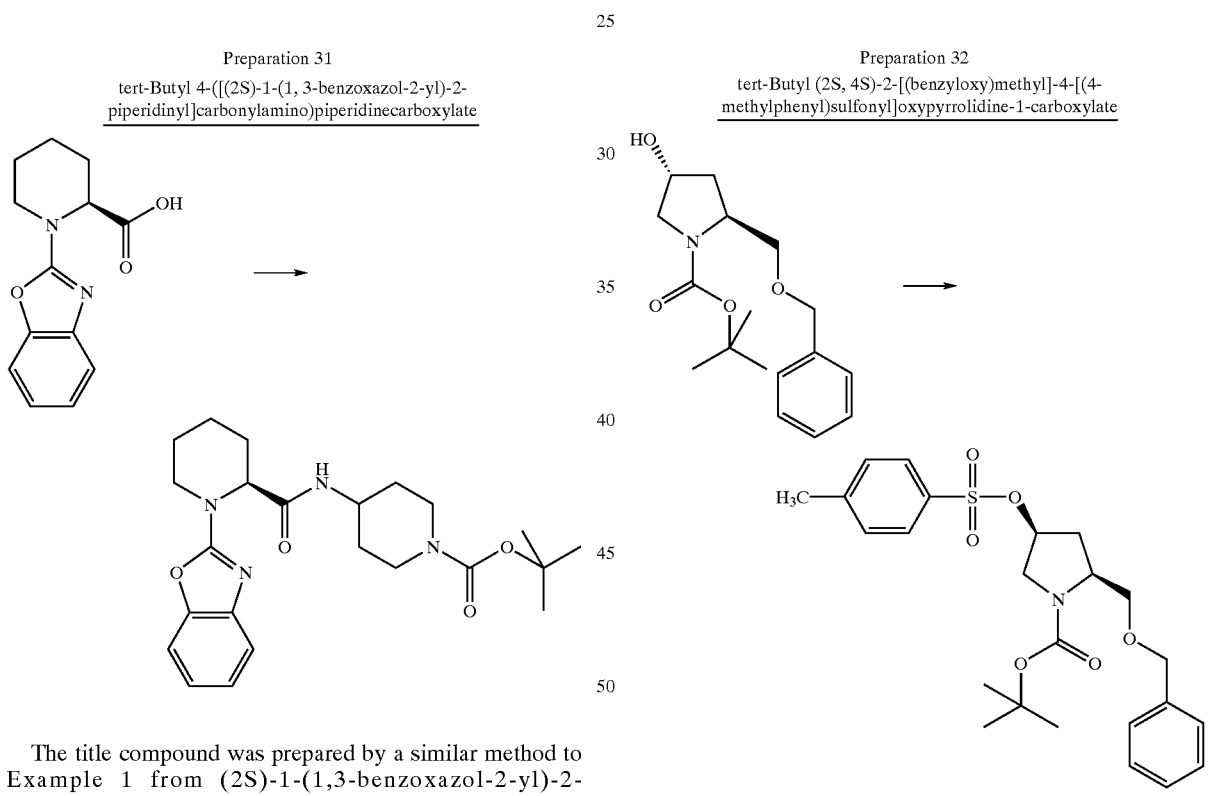 | MS: 276 (MH+). R$_f$: 0.12 (10:1, by volume, chloroform:methanol). |
| 30 | 23 | | MS: 231 (MH+). |

Preparation 31
tert-Butyl 4-([(2S)-1-(1, 3-benzoxazol-2-yl)-2-piperidinyl]carbonylamino)piperidinecarboxylate

Preparation 32
tert-Butyl (2S, 4S)-2-[(benzyloxy)methyl]-4-[(4-methylphenyl)sulfonyl]oxypyrrolidine-1-carboxylate The title compound was prepared by a similar method to Example 1 from (2S)-1-(1,3-benzoxazol-2-yl)-2-piperidinecarboxylic acid [see Preparation 3] and tert-butyl 4-amino-1(2H)-piperidinecarboxylate [see Takatani, Muneo et al, WO 9740051]. The crude product was purified by column chromatography on silica gel eluting with a solvent gradient of 2:1:0 changing to 0:95:5, by volume, hexane-:ethyl acetate:methanol to afford tert-butyl 4-([(2S)-1-(1,3-benzoxazol-2-yl)-2-piperidinyl]carbonylamino)piperidinecarboxylate as a white foam.

$^1$H-NMR (CDCl$_3$) δ: 7.40 (1H, m), 7.30 (1H, m), 7.20 (1H, m), 7.10 (1H, m), 6.40 (1H, d), 4.90 (1H, s), 4.30 (1H, d), 4.00 (3H, m), 3.20 (1H, t), 2.90 (2H, m), 2.40 (1H, d), 1.90 (2H, m), 1.80–1.60 (5H, m), 1.40 (9H, s), 1.30 (2H, m). MS: 429 (MH+).

Methyl 4-methyl-1-benzenesulfonate (0.8 g), triphenylphosphine (1.12 g) and diethyl azodicarboxylate (0.68 ml) were added sequentially to a solution of tert-butyl (2S,4R)-2-[(benzyloxy)methyl]-4-hydroxy-1-pyrrolidine-1-carboxylate (1.1 g) [see Takano, Seiichi, et al, J. Chem. Soc. Chem Commun. (1988), 23, 1527–1528] in dry tetrahydrofuran (10 ml) at 10° C. under a atmosphere of nitrogen. The reaction mixture was then stirred at room temperature for 48 hours, after which time the solvent was removed under reduced pressure and the residue partitioned between ethyl acetate and water. The organic layer was separated, dried over magnesium sulphate and the solvent removed under reduced pressure. The crude product was purified by column chromatography on silica gel eluting with a solvent system of 85:15, by volume, hexane:ethyl acetate to afford the title compound as a colourless gum.

¹H-NMR (CDCl₃) δ: 7.80 (2H, d), 7.30 (7H, m), 5.05 (1H, m), 4.50 (2H, m), 4.00 (1H, m), 3.70 (2H, m), 3.50 (2H, m), 2.50 (3H, s), 2.40–2.20 (2H, m), 1.45 (9H, s). MS: 462 (MH+).

Preparation 33
tert-Butyl (2S, 4R)-4-azido-2-[(benzyloxy)methyl] pyrrolidine-1-carboxylate

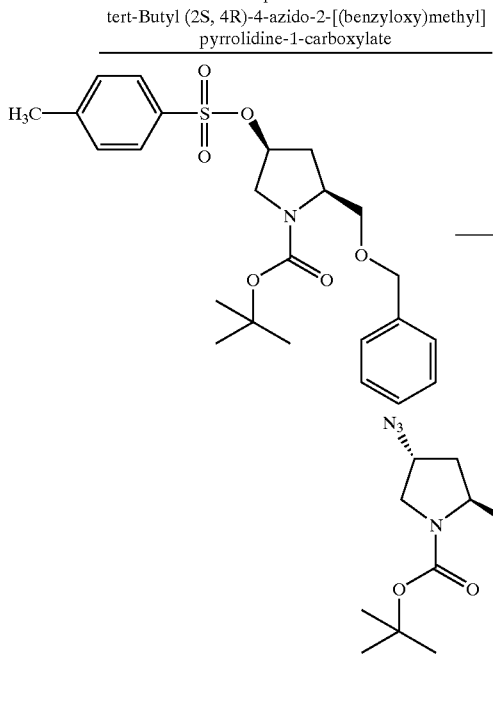

Sodium azide (0.32 g) was added to a solution of tert-Butyl (2S,4S)-2-[(benzyloxy)methyl]-4-[(4-methylphenyl)sulfonyl]oxypyrrolidine-1-carboxylate (1.15 g) [see Preparation 32] in ethanol (20 ml) and dimethylformamide (5 ml). The reaction mixture was heated to 80° C. for 4 hours, after which time the cooled mixture was partitioned between diethyl ether and water. The organic layer was separated and the aqueous extracted twice with diethyl ether, the combined organic layers were dried over magnesium sulphate and the solvent removed under reduced pressure. The residue was azeotroped with dichloromethane to afford tert-butyl (2S, 4R)-4-azido-2-[(benzyloxy)methyl]pyrrolidine-1-carboxylate (820 mg) as an oil.

¹H-NMR (CDCl₃) δ: 7.30 (5H, m), 4.50 (2H, s), 4.20–4.00 (2H, m), 3.70–3.40 (4H, m), 2.25 (1H, m), 2.15 (1H, m), 1.45 (9H, m). MS: 333 (MH+).

Preparation 34
tert-Butyl (2S, 4R)-4-amino-2-[(benzyloxy) methyl]pyrrolidine-1-carboxylate

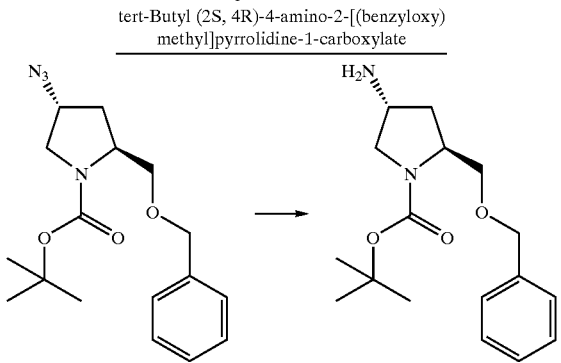

Triphenylphosphine (421 mg) was added to a solution of tert-butyl (2S,4R)-4-azido-2-[(benzyloxy)methyl]pyrrolidine-1-carboxylate (455 mg) [see Preparation 33] in dry tetrahydrofuran (10 ml). The reaction mixture was then stirred until the evolution of nitrogen gas had ceased, water (0.036 ml) was added, the mixture was then stirred for a further 72 hours. The solvent was then removed under reduced pressure and the residue was dissolved in diethyl ether and hexane added until the mixture became cloudy. The supernatant liquid was separated and the solvent removed under reduced pressure. The crude product was purified by column chromatography on silica gel eluting with a solvent system of 90:10, by volume, dichloromethane:methanol to afford tert-butyl (2S,4R)-4-amino-2-[(benzyloxy)methyl]pyrrolidine-1-carboxylate (225 mg) as a colourless oil.

¹H-NMR (CDCl₃) δ: 7.30 (5H, m), 4.55 (2H, s), 4.10 (1H, m), 3.70–3.40 (4H, m), 3.10 (1H, m), 2.25 (1H, m), 1.80 (1H, m), 1.50 (9H, m). MS: 307 (MH+).

Preparation 35
(3R)-1-(2-Pyridinylmethyl)-3-piperidinol

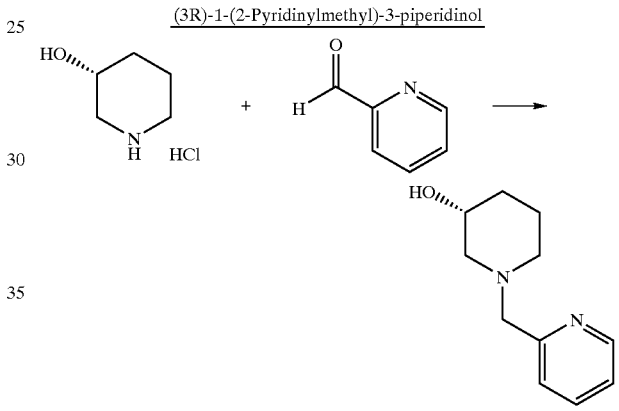

(3R)-3-Piperidinol hydrochloride (10.0 g) and triethylamine (10.13 ml) in dry 1,2-dichloroethane (350 ml) were stirred for 15 minutes at 50° C. 2-Pyridine carboxaldehyde (7.63 ml) and glacial acetic acid (4.16 ml) were added and the reaction mixture stirred for 1.5 hours at reflux. Sodium triacetoxyborohydride (34.65 g) was then added portionwise and the resulting mixture was cooled to room temperature and stirred for a further 1 hour. Water (350 ml) and 1M aqueous sodium hydroxide solution were then added until the mixture was pH12. The organic layer was separated and the aqueous extracted with chloroform, the combined organic layers were dried over magnesium sulphate and the solvent was removed under reduced pressure. The crude product was purified by column chromatography on silica gel eluting with a solvent system of 95:5, by volume, chloroform:methanol to afford (3R)-1-(2-pyridinylmethyl)-3-piperidinol (8.10 g) as a brown oil.

¹H-NMR (CDCl₃) δ: 8.55–8.50 (1H, m), 7.65–7.60 (1H, m), 7.30–7.25 (1H, m), 7.15–7.10 (1H, m), 3.85–3.75 (1H, m), 3.60 (2H, s), 2.80–2.70 (1H, bs), 2.60–2.50 (1H, m), 2.50–2.40 (2H, bs), 2.40–2.25 (1H, m), 1.80–1.70 (1H, m), 1.70–1.60 (1H., m), 1.60–1.40 (2H, m). Rf: 0.26 (95:5 by volume, chloroform:methanol).

Preparation 36
Benzyl (2S, 4R)-4-hydroxy-2-(phenoxymethyl)pyrrolidine-1-carboxylate

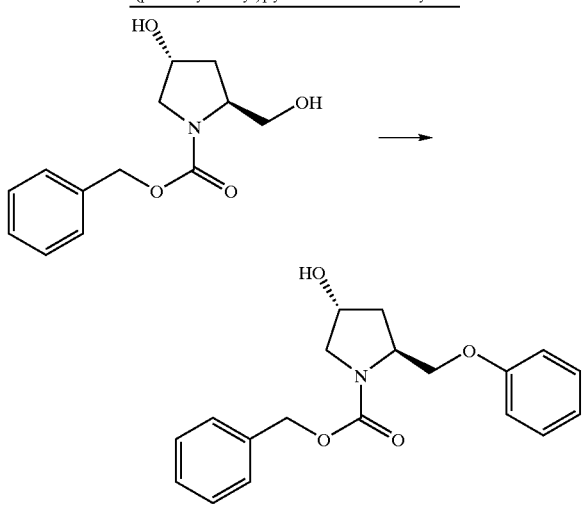

Benzyl (2S,4R)-4-hydroxy-2-(hydroxymethyl) pyrrolidine-1-carboxylate (2.0 g) [see Ceulemans et al, Chem. Eur. J. (1997), 3(12), 1997–2010] was added to a solution of phenol (1.12 g), triphenylphosphine (2.51 g) and diethylazodicarboxylate (1.51 ml) in dry tetrahydrofuran (40 ml). The reaction mixture was stirred at room temperature for 20 hours, after which time the solvent was removed under reduced pressure and the residue was dissolved in chloroform. The organic solution was washed with 15% aqueous sodium hydroxide solution, then brine, dried over magnesium sulphate and the solvent removed under reduced pressure. The crude product was purified by column chromatography on silica gel eluting with a solvent system of 1:1, by volume, hexane:ethyl acetate to afford benzyl (2S, 4R)-4-hydroxy-2-(phenoxymethyl)pyrrolidine-1-carboxylate (0.69 g) as a clear oil.

$^1$H-NMR (CDCl$_3$) δ: 7.40–7.20 (7H, m), 7.0–6.90 (1H, m), 6.85–6.75 (2H, d), 5.20–5.00 (3H, m), 4.80 (1H, s), 4.30–3.75 (2H, m), 3.75–3.60 (3H, m), 2.30–2.15 (1H, m), 2.10–2.00 (1H, m). Rf: 0.4 (1:1 by volume, hexane:ethyl acetate).

Preparation 37
(3R, 5S)-5-(Phenoxymethyl)pyrrolidin-3-ol

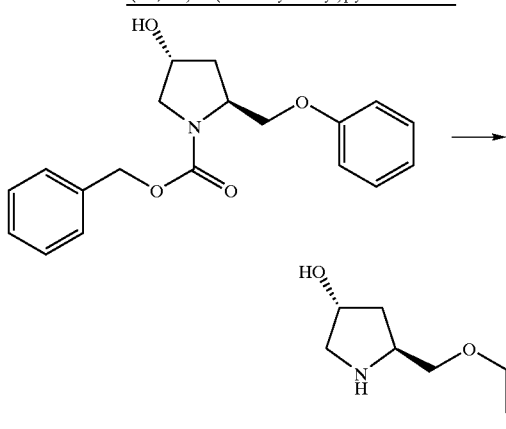

10% w/w Palladium on carbon (0.05 g) was added to a solution of benzyl (2S,4R)-4-hydroxy-2-(phenoxymethyl) pyrrolidine-1-carboxylate (0.25 g) [see Preparation 36] and 5M aqueous ammonium formate (1.45 ml) in methanol (20 ml).

The reaction mixture was heated under reflux for 3 days, after which time the reaction was filtered through celite and the solvent removed under reduced pressure. The crude product was purified by column chromatography on silica gel eluting with a solvent system of 90:10:0.5, by volume, chloroform:methanol:0.88 aqueous ammonia solution to afford (3R,5S)-5-(phenoxymethyl)pyrrolidine-3-ol (0.25 g) as a brown oil.

$^1$H-NMR (CDCl$_3$) δ: 7.24–7.20 (2H, t), 6.91–6.85 (1H, t), 6.80–6.75 (2H, d), 4.78–4.71 (1H, m), 3.80–3.68 (2H, bs), 3.64–3.59 (1H, dd), 3.56–3.49 (1H, dd), 3.26–3.19 (1H, m), 3.19–3.16 (1H, d), 3.02–2.94 (1H, dd), 2.24–2.14 (1H, ddd), 1.70–1.60 (1H, ddd). MS: 194 (MH+).

Preparation 38
(3R, 5S)-5-(Phenoxymethyl)-1-(4-pyridinylmethyl)pyrrolidin-3-ol

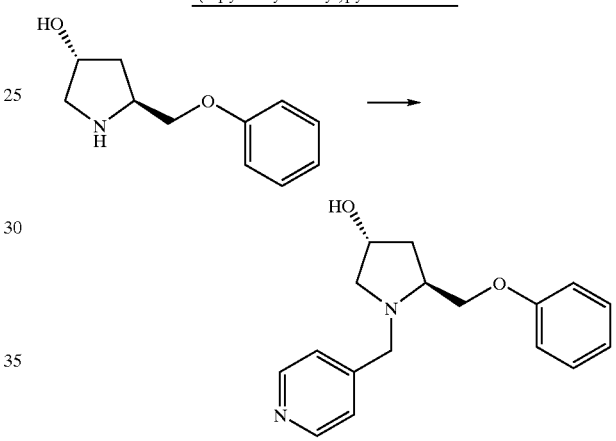

The title compound was prepared by a similar method to Preparation 35 from (3R,5S)-5-(phenoxymethyl) pyrrolidine-3-ol [see Preparation 37] and 4-pyridinecarboxaldehyde. The crude product was purified by column chromatography on silica gel eluting with a solvent system of 95:5, by volume, chloroform:methanol to afford (3R,5S)-5-(phenoxymethyl)-1-(4-pyridinylmethyl) pyrrolidine-3-ol as a white solid.

$^1$H-NMR (CDCl$_3$) δ: 8.45–8.40 (2H, m), 7.25–7.10 (4H, m), 6.90–6.80 (1H, m), 6.80–6.70 (2H, m), 4.73–4.66 (1H, m), 4.08–4.02 (1H, d), 3.73–3.66 (1H, dd), 3.56–3.50 (1H, dd), 3.36–3.28 (1H, d), 3.20–3.13 (2H, d), 2.87–2.80 (1H, m), 2.53–2.46 (1H, dd), 2.43–2.35 (1H, m), 2.12–2.03 (1H, m). Rotation: [◊]$_D^{25}$=−12.50° (c=1.0, chloroform). MS: 285 (MH+).

Preparation 39
(3R)-1-[(Fluoro-4-pyridinyl)methyl]-3-piperidinol

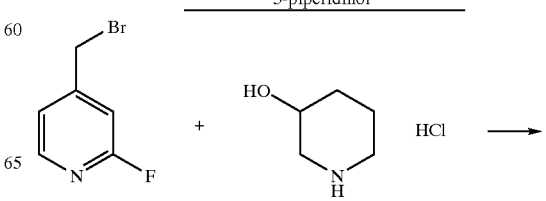

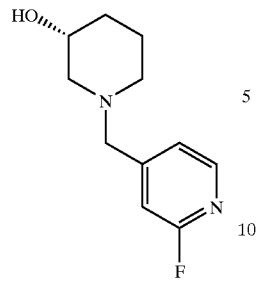

(3R)-3-hydroxypiperidine hydrochloride (0.188 g) was added to a solution of 4-(bromomethyl)-2-fluoropyridine (0.26 g) [see Porter et al, WO 9622978] and potassium carbonate (0.189 g) in acetonitrile (15 ml). The reaction mixture was refluxed for 5 days, after which time the solvent was removed under reduced pressure and the residue partitioned between dichloromethane and water. The organic layer was separated and the aqueous was adjusted to pH 12 and the product extracted with dichloromethane. The combined organic layers were dried over magnesium sulphate and the solvent removed under reduced pressure. The crude product was purified by column chromatography on silica gel eluting with a solvent system of 95:5, by volume, chloroform:methanol to afford (3R)-1-[(2-fluoro-4-pyridinyl)methyl]-3-piperidinol (0.255 g) as a pale yellow oil.

$^1$H-NMR (CDCl$_3$) δ: 7.97–7.96 (1H, d), 7.03–7.01 (1H, d), 6.80 (1H, s), 3.70–3.60 (1H, m), 3.44–3.36 (2H, m), 3.32 (1H, s), 2.55–2.45 (1H, d), 2.35–2.20 (1H, bs), 2.20–2.05 (2H, d), 1.70–1.60 (2H, d), 1.50–1.35 (1H, m), 1.35–1.25 (1H, m). MS: 211 (MH+).

Preparation 40
tert-Butyl N-[(3S)-1-(3-pyridinylmethyl) pyrrolidin-3-yl]carbamate

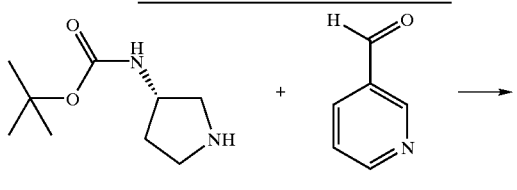

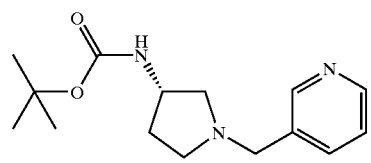

The title compound was prepared by a similar method to Preparation 7 from tert-butyl N-[(3S)-1-pyrrolidine-3-yl]carbamate (see J. Het. Chem., 1990, 27, 1286–1287) and 3-pyridinecarboxaldehyde to afford tert-butyl N-[(3S)-1-(3-pyridinylmethyl)pyrrolidine-3-yl]carbamate which was used immediately for Preparation 41.

Preparation 41
(3S)-1-(3-Pyridinylmethyl) pyrrolidine-3-amine

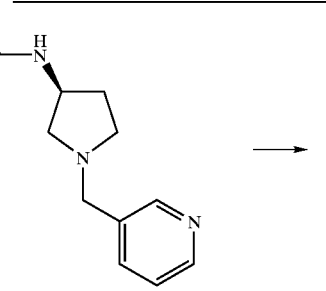

The title compound was prepared by a similar method to Preparation 8 from tert-butyl N[(3S)-1-(3-pyridinylmethyl)-1-pyrrolidine-3-yl]carbamate (see Preparation 40] and hydrogen chloride to afford (3S)-1-(3-pyridinylmethyl) pyrrolidine-3-amine as a white solid.

MS: 178 (MH$^+$).

Preparation 42
Ethyl (2S)-1-(1, 3-benzothiazol-2-yl)-2-piperidinecarboxylate

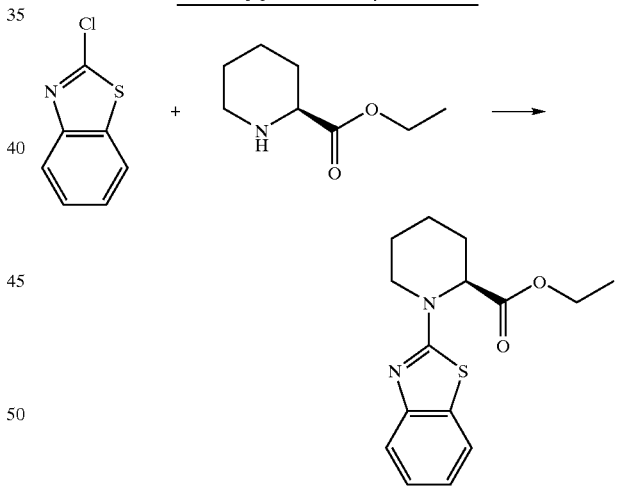

2-Chloro-1,3-benzothiazole (503 mg) was added to a suspension of ethyl (2S)-2-piperidinecarboxylate (471 mg) [J.A.C.S. (1993), 115(22), 9925–9938], triethylamine hydrochloride (414 mg) and copper powder (38 mg) in xylene (5 ml). The reaction mixture was refluxed for 28 hours, after which time ethyl acetate (20 ml) was added to the cooled mixture and the solids filtered off. The organic layer was washed with water, dried over magnesium sulphate and the solvent removed under reduced pressure to afford ethyl (2S)-1-(1,3-benzothiazol-2-yl)-2-piperidinecarboxylate (705 mg) as a brown solid.

$^1$H-NMR (CDCl$_3$) δ: 7.58 (1H, d), 7.50 (1H, d), 7.20 (1H, t), 7.00 (1H, t), 5.10 (1H, d), 4.18 (2H, q), 3.80 (1H, m), 3.42

(1H, m), 2.25 (1H, d), 1.95–1.80 (3H, m), 1.60 (1H, m), 1.40 (1H, m), 1.20 (3H, t). MS: 291 (MH+).

Preparation 43
(2S)-1-(1, 3-Benzothiazol-2-yl)-2-piperidinecarboxylic acid

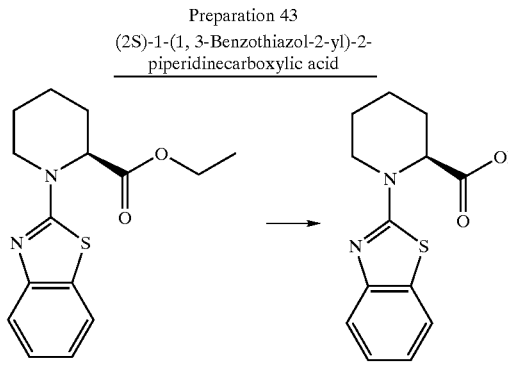

The title compound was prepared by a similar method to Preparation 3 from ethyl (2S)-1-(1,3-benzothiazol-2-yl)-2-piperidinecarboxylate [see Preparation 42] and 1N aqueous lithium hydroxide solution. The crude product was purified by column chromatography on silica gel eluting with a solvent system of 10:1, by volume, dichloromethane:methanol to afford (2S)-1-(1,3-benzothiazol-2-yl)-2-piperidinecarboxylic acid as a solid.

$^1$H-NMR (CDCl$_3$) δ: 7.42 (2H, m), 7.10 (1H, m), 6.95 (1H, m), 4.80 (1H, m), 3.50 (2H, m), 2.10 (1H, m), 1.50 (5H, m). MS: 261 (MH+).

Preparation 44
Ethyl (2S)-1-(6-chloro-1, 3-benzothiazol-2-yl)-2-piperidinecarboxylate

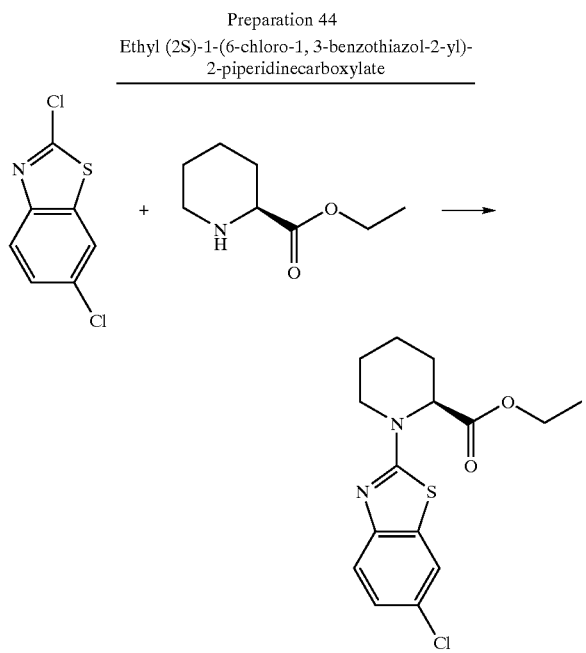

The title compound was prepared by a similar method to Preparation 42 from 2,6-dichloro-1,3-benzothiazole [see J. Ind. Chem. Soc., (1993), 10, 565–569] and ethyl (2S)-2-piperidinecarboxylate (471 mg) [see J.A.C.S. (1993), 115 (22), 9925–9938] to afford ethyl (2S)-1-(6-chloro-1,3-benzothiazol-2-yl)-2-piperidinecarboxylate as a solid.

$^1$H-NMR (CDCl$_3$) δ: 7.55 (1H, s), 7.40 (1H, d), 7.15 (1H, d), 5.05 (1H, d), 4.15 (2H, q), 3.65 (1H, m), 3.45 (1H, m), 2.22 (1H, m), 1.80 (2H, m), 1.60 (1H, m), 1.35 (1H, m), 1.15 (3H, t). MS: 325 (MH+).

Preparation 45
(2S)-1-(6-Chloro-1, 3-benzothiazol-2-yl)-2-piperidinecarboxylic acid

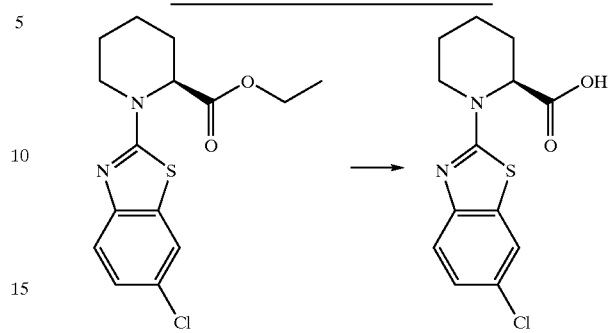

The title compound was prepared by a similar method to Preparation 3 from ethyl (2S)-1-(6-chloro-1,3-benzothiazol-2-yl)-2-piperidinecarboxylate [see Preparation 44] and 1N aqueous lithium hydroxide solution to afford (2S)-1-(6-chloro-1,3-benzothiazol-2-yl)-2-piperidinecarboxylic acid as a solid.

$^1$H-NMR (DMSO-d$_6$) δ: 7.80 (1H, s), 7.70 (1H, d), 7.30 (1H, d), 5.60 (1H, bs), 4.75 (1H, bs), 3.40 (2H, m), 2.20 (1H, m), 1.80–1.60 (3H, m), 1.50 (1H, m), 1.30 (1H, m). MS: 295 (MH+).

Preparation 46
tert-Butyl 2-chloro-1H-1, 3-benzimidazole-1-carboxylate

2-Chloro-1H-1,3-benzimidazole (1.07 g) was added to a solution of di-tert-butyldicarbonate (1.83 g) and 4-dimethylaminopyridine (86 mg) in acetonitrile (15 ml). The reaction mixture was stirred at room temperature for 30 minutes, after which time the solvent was removed under reduced pressure. The crude product was then purified by column chromatography on silica gel eluting with a solvent gradient of 100:0 changing to 90:10, by volume, hexane::ethyl acetate to afford tert-butyl 2-chloro-1H-1,3-benzimidazole-1-carboxylate (1.68 g) as a white solid.

$^1$H-NMR (CDCl$_3$) δ: 7.90 (1H, m), 7.35 (1H, m), 7.40 (2H, m), 1.80 (9H, s). MS: 253 (MH+).

Preparation 47
tert-Butyl 2-[(2S)-2-[(benzyloxy)carbonyl]-1-piperidinyl]-1H-1, 3-benzimidazole-1-carboxylate

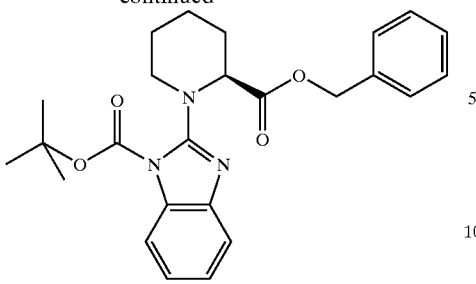

The title compound was prepared by a similar method to Preparation 2 from tert-butyl 2-chloro-1H-1,3-benzimidazole-1-carboxylate [see Preparation 46] and benzyl (2S)-2-piperidinecarboxylate [see J.A.C.S. (1 996), 118 (7), 1629–1644]. The crude product was purified by column chromatography on silica gel eluting with a solvent gradient of 90:10 changing to 80:20, by volume, hexane:ethyl acetate, in 5% increments to afford tert-butyl 2-[(2S)-2-[(benzyloxy)carbonyl]-1-piperidinyl]-1H-1,3-benzimidazole-1-carboxylate as an oil.

$^1$H-NMR (CDCl$_3$) δ: 7.65 (1H, d), 7.45 (1H, d), 7.40 (2H, s), 7.25 (5H, m), 5.20 (2H, s), 4.70 (1H, m), 4.65 (1H, m), 3.60 (1H, m), 2.20 (1H, m), 2.05 (1H, m), 1.80–1.50 (13H, m). MS: 436 (MH+).

Preparation 48
(2S)-1-[1-tert-Butoxycarbonyl)-1H-1,3-benzimidazol-2-yl]-2-piperidinecarboxylic

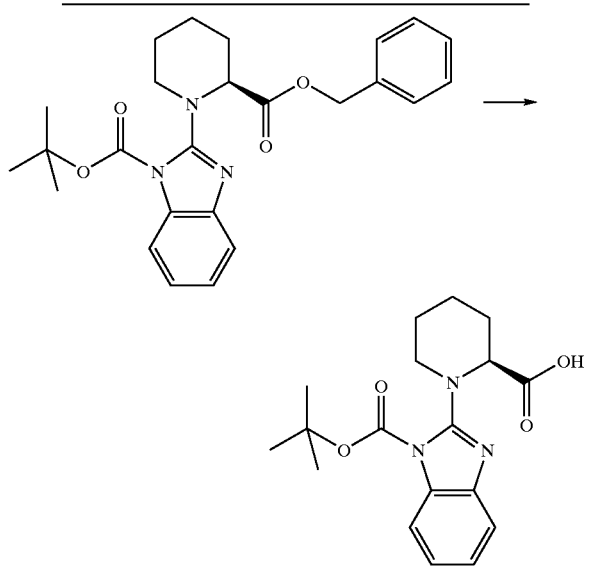

10% w/w Palladium on carbon (300 mg) was added to a solution of tert-butyl 2-[(2S)-2-[(benzyloxy)carbonyl]-1-piperidinyl]-1H-1,3-benzimidazole-1-carboxylate (900 mg) [see Preparation 47] in ethanol (30 ml). The reaction mixture was hydrogenated at 103.5 kPa (15 psi) at room temperature for 18 hours. The catalyst was then filtered off and the solvent removed under reduced pressure to afford (2S)-1-[1-(tert-butoxycarbonyl)-1H-1,3-benzimidazol-2-yl]-2-piperidinecarboxylic acid (700 mg) as a white foam.

$^1$H-NMR (DMSO-d$_6$) δ: 7.65 (1H, d), 7.35 (1H, d), 7.20 (1H, t), 7.10 (1H, t), 4.40 (1H, m), 3.50 (2H, m), 2.05 (1H, d), 1.90 (1H, m), 1.70–1.40 (13H, m).

Preparation 49
1,3,4, 12a-Tetrahydropyrido[1',2':3,4]imidazo[1,2-a][1,3]benzimidazol-12(2H)-

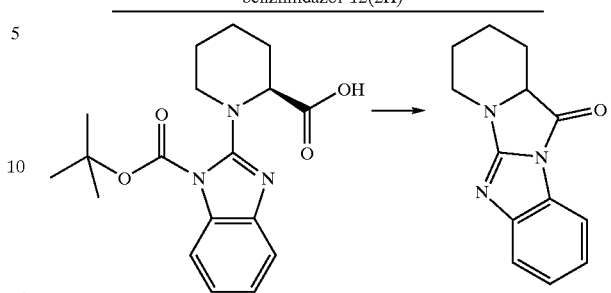

The title compound was prepared by a similar method to Example 1 from (2S)-1-[1-(tert-butoxycarbonyl)-1H-1,3-benzimidazol-2-yl]-2-piperidinecarboxylic acid [see Preparation 48] and (3S)-1-benzylpyrrolidin-3-ylamine. The crude product was purified by column chromatography on silica gel eluting with a solvent gradient of 70:30 changing to 50:50, by volume, hexane:ethyl acetate followed by 90:10:1, dichloromethane:methanol:0.88 ammonia to afford 1,3,4,12a-tetrahydropyrido[1',2':3,4]imidazo[1,2-a][1,3]benzimidazol-12(2H)-one as a white solid.

$^1$H-NMR (CDCl$_3$) δ: 7.60 (1H, d), 7.40 (1H, d), 7.30 (1H, m), 7.10 (1H, t), 4.20 (2H, m), 3.20 (1H, m), 2.35 (1H,d), 2.05 (1H, m), 1.80 (1H, d), 1.70–1.50 (3H, m). MS: 227 (MH$^+$).

It will be appreciated that what will be claimed is as follows:

(i) a compound of the formula (I) or a pharmaceutically acceptable salt or solvate thereof;

(ii) a process for the preparation of a compound of the formula (I) or a pharmaceutically acceptable salt or solvate thereof;

(iii) a pharmaceutical composition comprising a compound of the formula (I) or a pharmaceutically acceptable salt or solvate thereof, together with a pharmaceutically acceptable excipient, diluent or carrier;

(iv) a compound of the formula (I) or a pharmaceutically acceptable salt, solvate or composition thereof, for use as a medicament;

(v) the use of a compound of the formula (I) or of a pharmaceutically acceptable salt, solvate or composition thereof, for the manufacture of a medicament for the treatment of neuronal degeneration;

(vi) the use of a compound of the formula (I) or of a pharmaceutically acceptable salt, solvate or composition thereof, for the manufacture of a medicament for the promotion of neuronal regeneration and outgrowth;

(vii) the use of a compound of the formula (I) or of a pharmaceutically acceptable salt, solvate or composition thereof, for the manufacture of a medicament for the treatment of a neurological disease or disorder such as a neurodegenerative disease;

(viii) use as in (vii) where the neurological disease or disorder is selected from the group consisting of senile dementia (Alzheimer's disease) and other dementias, amyotrophic lateral sclerosis and other forms of motor neuron disease, Parkinson's disease, Huntington's disease, neurological deficits associated with stroke, all forms of degenerative disease affecting the central or peripheral nervous system (e.g. cerebellar-brainstem atrophies, syndromes of progressive ataxias), all forms of muscular dystrophy, progressive muscular atrophies, progressive bulbar muscular atrophy, physical or traumatic damage to the central or peripheral nervous system (e.g. spinal cord), herniated, ruptured or prolapsed intervertebrae disc syndromes, cervical spondylosis, plexus disorders, thoracic outlet syndromes, all forms of peripheral neuropathy (both diabetic and non-diabetic), trigeminal neuralgia, glossopharyngeal neuralgia, Bell's Palsy, all forms of auto-immune related disease resulting in damage of the central or peripheral nervous system (e.g. multiple sclerosis, myasthenia gravis, Guillain-Barré syndrome), AIDS related disorders of the nervous system, dapsone ticks, bulbar and retrobulbar affections of the optic nerve (e.g. retinopathies and retrobulbar neuritis), hearing disorders such as tinnitus, and prion diseases;

(ix) use as (viii) where the neurological disease or disorder is senile dementia (Alzheimer's disease) or another dementia, amyotrophic lateral sclerosis or another form of motor neuron disease, Parkinson's disease, Huntington's disease, a neurological deficit associated with stroke, physical or traumatic damage to the central or peripheral nervous system (e.g. spinal cord), a peripheral neuropathy (either diabetic or non-diabetic), multiple sclerosis or a hearing disorder such as tinnitus;

(x) a method of treatment of a human to treat neuronal degeneration which comprises treating said human with an effective amount of a compound of the formula (I) or with a pharmaceutically acceptable salt, solvate or composition thereof;

(xi) a method of treatment of a human to promote neuronal regeneration and outgrowth which comprises treating said human with an effective amount of a compound of the formula (I) or with a pharmaceutically acceptable salt, solvate or composition thereof;

(xii) a method of treatment of a human to treat a neurological disease or disorder such as a neurodegenerative disease which comprises treating said human with an effective amount of a compound of the formula (I) or with a pharmaceutically acceptable salt, solvate or composition thereof;

(xiii) a method as in (xii) where the neurological disease or disorder is selected from the group consisting of senile dementia (Alzheimer's disease) and other dementias, amyotrophic lateral sclerosis and other forms of motor neuron disease, Parkinson's disease, Huntington's disease, neurological deficits associated with stroke, all forms of degenerative disease affecting the central or peripheral nervous system (e.g. cerebellar-brainstem atrophies, syndromes of progressive ataxias), all forms of muscular dystrophy, progressive muscular atrophies, progressive bulbar muscular atrophy, physical or traumatic damage to the central or peripheral nervous system (e.g. spinal cord), herniated, ruptured or prolapsed intervertebrae disc syndromes, cervical spondylosis, plexus disorders, thoracic outlet syndromes, all forms of peripheral neuropathy (both diabetic and non-diabetic), trigeminal neuralgia, glossopharyngeal neuralgia, Bell's Palsy, all forms of autoimmune related disease resulting in damage of the central or peripheral nervous system (e.g. multiple sclerosis, myasthenia gravis, Guillain-Barré syndrome), AIDS related disorders of the nervous system, dapsone ticks, bulbar and retrobulbar affections of the optic nerve (e.g. retinopathies and retrobulbar neuritis), hearing disorders such as tinnitus, and prion diseases;

(xiv) a method as in (xiii) where the neurological disease or disorder is senile dementia (Alzheimer's disease) or another dementia, amyotrophic lateral sclerosis or another form of motor neuron disease, Parkinson's disease, Huntington's disease, a neurological deficit associated with stroke, physical or traumatic damage to the central or peripheral nervous system (e.g. spinal cord), a peripheral neuropathy (either diabetic or non-diabetic), multiple sclerosis or a hearing disorder such as tinnitus; and (xv) any novel intermediates described herein.

(xvi) the use of a compound of the formula (I) or of a pharmaceutically acceptable salt, solvate or composition thereof, for the manufacture of a medicament for the treatment of a disease resulting from a deficiency or over production of FKBP-12 or FKBP-52.

The compounds of the invention demonstrate inhibitory activity against the rotamase enzyme FKBP-12. In particular some of the better compounds i.e. the compounds of examples 2, 6, 7, 8, 13a, 15, 16, 17, 18, 19, 20, 21, 22, 23, 24, 25, 26, 27, 30, 35 and 41 were found to have an $IC_{50}$ for inhibition of the FKBP-12 enzyme of below 1200 nM. The compound of example 2 was found to have an $IC_{50}$ for inhibition of the FKBP-52 enzyme of 2790 nM.

What is claimed is:

1. A compound having the general formula (IX):

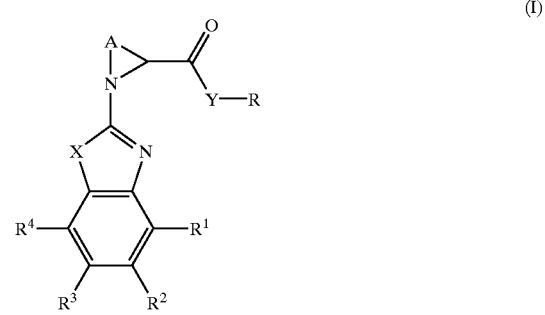

(I)

wherein $R^1$, $R^2$, $R^3$ and $R^4$ are each independently selected from H, halo, $C_1$–$C_6$ alkyl, $C_3$–$C_7$ cycloalkyl, halo($C_1$–$C_6$) alkyl, $C_1$–$C_6$ alkoxy, —$CONR^5R^6$, $C_3$–$C_7$ cycloalkoxy, $C_3$–$C_7$ cycloalkyl($C_2$–$C_4$)alkylene, $C_3$–$C_7$ cycloalkyl($C_2$–$C_4$)alkoxy and —$CO_2(C_1$–$C_6$ alkyl);

$R^5$ and $R^6$ are either each independently selected from H and C1–C6alkyl or, when taken together, represent unbranched $C_3$–$C_5$ alkylene;

$R^8$ is a $C_1$ to $C_4$ alkyl or benzyl group and wherein $L^2$ is a suitable leaving group.

2. A compound of the formula (XI):

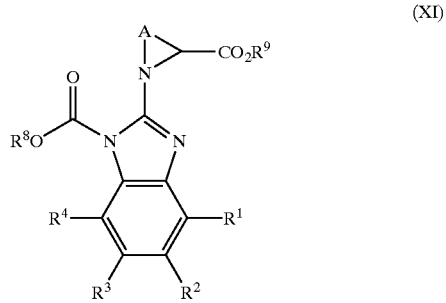

(XI)

wherein A is unbranched $C_3$–$C_5$ alkylene optionally substituted by $C_1$–$C_6$ alkyl;

$R^1$, $R^2$, $R^3$ and $R^4$ are each independently selected from H, halo, $C_1$–$C_6$ alkyl, $C_3$–$C_7$ cycloalkyl, halo($C_1$–$C_6$) alkyl, $C_1$–$C_6$ alkoxy, —$CONR^5R^6$, $C_3$–$C_7$ cycloalkoxy, $C_3$–$C_7$ cycloalkyl-($C_2$–$C_4$)alkylene, $C_3$–$C_7$ cycloalkyl($C_2$–$C_4$)alkoxy and —$CO_2$($C_1$–$C_6$ alkyl);

$R^5$ and $R^6$ are either each independently selected from H and $C_1$–$C_6$alkyl or, when taken together, represent unbranched $C_3$–$C_5$ alkylene;

$R^8$ is a $C_1$–$C_4$ alkyl or benzyl group;

and $R^9$ is a $C_1$–$C_4$ alkyl or benzyl group.

3. A compound of the formula (XII):

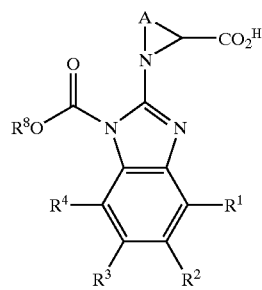

wherein A is unbranched $C_3$–$C_5$ alkylene optionally substituted by $C_1$–$C_6$ alkyl;

$R^1$, $R^2$, $R^3$ and $R^4$ are each independently selected from H, halo, $C_1$–$C_6$ alkyl, $C_3$–$C_7$ cycloalkyl, halo($C_1$–$C_6$) alkyl, $C_1$–$C_6$ alkoxy, —$CONR^5R^6$, $C_3$–$C_7$ cycloalkoxy, $C_3$–$C_7$ cycloalkyl-($C_2$–$C_4$)alkylene, $C_3$–$C_7$ cycloalkyl($C_2$–$C_4$)alkoxy and —$CO_2$($C_1$–$C_6$ alkyl);

$R^5$ and $R^6$ are either each independently selected from H and C1–C6 alkyl or, when taken together, represent unbranched $C_3$–$C_5$ alkylene;

and $R^8$ is a $C_1$–$C_4$ alkyl or benzyl group.

4. A compound of the formula (XIIIA) or (XIIIB):

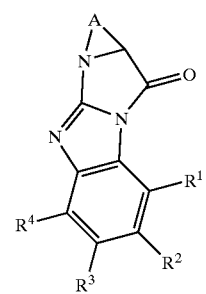

(XIIIA)

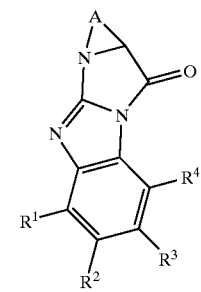

(XIIIB)

wherein A is unbranched $C_3$–$C_5$ alkylene optionally substituted by $C_1$–$C_6$ alkyl;

$R^1$, $R^2$, $R^3$ and $R^4$ are each independently selected from H, halo, $C_1$–$C_6$ alkyl, $C_3$–$C_7$ cycloalkyl, halo($C_1$–$C_6$) alkyl, $C_1$–$C_6$ alkoxy, —$CONR^5R^6$, $C_3$–$C_7$ cycloalkoxy, $C_3$–$C_7$ cycloalkyl-($C_2$–$C_4$)alkylene, $C_3$–$C_7$ cycloalkyl($C_2$–$C_4$)alkoxy and —$CO_2$($C_1$–$C_6$ alkyl);

and $R^5$ and $R^6$ are either each independently selected from H and C1–C6alkyl or, when taken together, represent unbranched $C_3$–$C_5$ alkylene.

* * * * *